United States Patent
Mukumoto

(10) Patent No.: US 9,757,075 B2
(45) Date of Patent: Sep. 12, 2017

(54) X-RAY CT SYSTEM

(71) Applicant: Toshiba Medical Systems Corporation, Otawara-shi (JP)

(72) Inventor: Go Mukumoto, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 19 days.

(21) Appl. No.: 13/980,505

(22) PCT Filed: Dec. 6, 2012

(86) PCT No.: PCT/JP2012/081684
§ 371 (c)(1),
(2) Date: Jul. 18, 2013

(87) PCT Pub. No.: WO2013/114728
PCT Pub. Date: Aug. 8, 2013

(65) Prior Publication Data
US 2014/0072097 A1 Mar. 13, 2014

(30) Foreign Application Priority Data

Feb. 2, 2012 (JP) ................ 2012-020431
Feb. 21, 2012 (JP) ................ 2012-035389
Dec. 5, 2012 (JP) ................ 2012-265951

(51) Int. Cl.
*A61B 6/03* (2006.01)
*A61B 6/04* (2006.01)
*A61B 6/00* (2006.01)

(52) U.S. Cl.
CPC ............. *A61B 6/03* (2013.01); *A61B 6/032* (2013.01); *A61B 6/0457* (2013.01); *A61B 6/547* (2013.01);
(Continued)

(58) Field of Classification Search
CPC ......... A61B 6/03; A61B 6/032; A61B 6/0457; A61B 6/487; A61B 6/504; A61B 6/541; A61B 6/547; A61B 6/5235; A61N 5/1049
(Continued)

(56) References Cited

U.S. PATENT DOCUMENTS 5,769,787 A * 6/1998 Lemelson ............ 600/407
6,049,281 A 4/2000 Osterweil
(Continued)

FOREIGN PATENT DOCUMENTS

CN 1686052 A 10/2005
JP 62 204728 9/1987
(Continued)

OTHER PUBLICATIONS

International Search Report Issued Mar. 5, 2013 in PCT/JP12/081684 Filed Dec. 6, 2012 (with Translation of Category).
(Continued)

*Primary Examiner* — Glen Kao
(74) *Attorney, Agent, or Firm* — Oblon, McClelland, Maier & Neustadt, L.L.P.

(57) ABSTRACT

An X-ray CT system is provided to achieve simplification and time-saving in the work of setting the subject in scanning position. An X-ray CT system as an embodiment comprises a patient table, a gantry apparatus, a formation unit, a drive unit, a storage unit, and a drive controller. The patient table has a top plate, on which the subject is placed. The gantry apparatus executes scanning on the subject by rotating a detector unit, which includes an X-ray tube and an X-ray detector set facing each other. The formation unit forms image data of the subject based on the data acquired by the scanning. The drive unit changes the relative position between the top plate and the detector unit. The storage unit stores relative position information that indicates the relative (Continued)

position applied for the scanning. When a new scanning session is to be performed, the drive controller controls the drive unit to set the top plate and the detector unit at the relative position indicated by the stored relative position information.

9 Claims, 15 Drawing Sheets

(52) U.S. Cl.
CPC .............. *A61B 6/487* (2013.01); *A61B 6/504* (2013.01); *A61B 6/5235* (2013.01); *A61B 6/541* (2013.01)

(58) Field of Classification Search
USPC ........ 378/4, 8, 19, 20, 68, 69, 95, 162, 163, 378/164, 165, 195, 204, 205, 208, 209
See application file for complete search history.

(56) References Cited

U.S. PATENT DOCUMENTS

| | | | |
|---|---|---|---|
| 6,935,780 B2* | 8/2005 | Barde et al. | 378/209 |
| 2002/0039403 A1 | 4/2002 | Oota | |
| 2006/0241387 A1 | 10/2006 | Nagamine et al. | |
| 2006/0291615 A1 | 12/2006 | Nishide et al. | |
| 2008/0016620 A1* | 1/2008 | Haras | 5/601 |
| 2008/0144772 A1* | 6/2008 | Yi et al. | 378/65 |
| 2009/0161821 A1* | 6/2009 | Klingenbeck-Regn | 378/20 |
| 2009/0245457 A1* | 10/2009 | Takeuchi et al. | 378/8 |
| 2011/0286574 A1* | 11/2011 | Suzuki | 378/8 |

FOREIGN PATENT DOCUMENTS

| | | |
|---|---|---|
| JP | 63 222740 | 9/1988 |
| JP | 1-97438 A | 4/1989 |
| JP | 6-86778 A | 3/1994 |
| JP | 2002 102220 | 4/2002 |
| JP | 2003-102717 | 4/2003 |
| JP | 2003-126076 A | 5/2003 |
| JP | 2005-223776 | 8/2005 |
| JP | 2007 408 | 1/2007 |
| JP | 2008-228828 A | 10/2008 |
| JP | 2011 004980 | 1/2011 |
| JP | 2011-244846 A | 12/2011 |
| WO | 2006/077869 A1 | 7/2006 |

OTHER PUBLICATIONS

Combined Office Action and Search Report issued Mar. 17, 2015 in Chinese Patent Application No. 201280008746.6 (with English translation of Category of Cited Documents).
Office Action dated Aug. 23, 2016, in Japanese Patent Application No. 2012-265951.
Office Action issued Jan. 5, 2016 in Japanese Patent Application No. 2012-035389.

* cited by examiner

X-RAY CT SYSTEM

TECHNICAL FIELD

Embodiments of the present invention relate to X-ray CT systems.

BACKGROUND ART

X-ray CT (Computed Tomography) systems are a system that provides imaging of the interior of a subject by scanning the subject with X-ray equipment for data acquisition, and then by processing the gathered data with a computer.

Specifically, an X-ray CT system makes X-ray exposures on the subject multiple times in different directions, detects the X-rays that have passed through the subject with an X-ray detector, and acquires multiple sets of data during the detection. The detection data gathered are A/D converted by a data acquisition system and then sent to a data-processing system. The data-processing system executes preprocessing, etc. on the detection data to form projection data. Following this process, the data-processing system executes reconstruction-processing on the projection data to form tomographic data. In addition, based on multiple sets of tomographic data, the data-processing system executes further reconstruction-processing to form a volumetric data. Volumetric data are a data set that represents a three-dimensional distribution of CT values that correspond to the three-dimensional scanned region of the subject.

The X-ray CT system enables MPR (Multi Planar Reconstruction) display by rendering the volumetric data in a given direction. MPR-processed sectional images (MPR images) include three-orthogonal-axis images and oblique images. The three-orthogonal-axis images include axial images showing sections perpendicular to the axis of the body, sagittal images showing sections dividing the subject vertically along the body axis, and coronal images showing sections dividing the subject horizontally along the body axis. The oblique images are those showing sections that are not shown in three-orthogonal-axis images. In addition, the X-ray CT system produces, by rendering the volumetric data with a parameter of arbitrary eyeline, a pseudo-three-dimensional image as a view of the three-dimensional part of the subject being looked at along the eyeline.

There is a scanning method called "CT fluoroscopy" (CTF: Computed Tomography Fluoroscopy). CT fluoroscopy is a scanning method for acquiring in real time an image of the region of interest of the subject by exposing the subject to X-ray radiation continually or intermittently. In CT fluoroscopy, the rate of detection data gathering is quickened, and the time required for reconstruction-processing is shortened for real-time image generation. CT fluoroscopy is applied for monitoring purpose, for example, in a biopsy where the positional relation between the puncture needlepoint and the living tissue to be examined is monitored or in a drainage where the position of the tube used for draining fluid is monitored. By the way, the drainage herein is a method for draining bodily fluids that have accumulated in body cavities by using, for example, a tube.

During a CT fluoroscopy, actions of scanning and of medical procedure may be performed repeatedly one after the other. For example, in a case where a biopsy is performed, while reference is being made to MPR images based on volumetric data provided in CT fluoroscopy, scanning and puncturing are performed repeatedly one after the other. Specifically, at first, the subject is set in a predetermined scanning position, and an MPR image of the subject is achieved by CT fluoroscopy. Then, the subject is moved from the scanning position to a predetermined procedural position, and there, puncturing is performed while the MPR image is being referred to. After the puncture needle has been inserted to some extent, the subject is set in the scanning position again for another session of CT fluoroscopy in order to acquire a new MPR image. After that, the subject is set in the procedural position again, and the puncturing is further advanced with reference to this new MPR image. These actions are repeated until the biopsy is complete. In some other cases, a puncturing plan is made for determining a course for insertion of a puncture needle before actual puncturing is performed. Such planning also involves scanning.

PRIOR ART REFERENCES

Patent References

[Patent reference 1] Japanese Laid-Open Patent Publication No. 2011-4980
[Patent reference 2] Japanese Laid-Open Patent Publication No. 2007-000408

SUMMARY OF THE INVENTION

Problems to be Solved by the Invention

In such a case as mentioned above, where the sessions of scanning and of medical procedure are repeated one after the other, one of the repeated actions is setting the subject in the scanning position, and another is setting the subject in the position where the medical procedure is performed. With prior-art X-ray CT systems, it has been necessary to make positional adjustments whenever the setting of the subject is switched between the scanning position and the position where the medical procedure is executed. The adjustment work, however, is complicated and time-consuming, and therefore, it has been a burden to the specialist and the patient.

The present invention is to solve this problem by providing an X-ray CT system that is capable of simplifying the work of setting the subject in desired positions and of shortening the time required for the work.

Means for Solving the Problems

An X-ray CT system as an embodiment comprises a patient table, a gantry apparatus, a formation unit, a drive unit, a storage unit, and a drive controller. The patient table has a top plate, on which a subject is placed. The gantry apparatus executes scanning on the subject by rotating a detector unit, which includes an X-ray tube and an X-ray detector set facing each other. The formation unit forms image data of the subject based on data acquired by the scanning. The drive unit changes the relative position between the top plate and the detector unit. The storage unit stores relative position information that indicates the relative position applied for the scanning. When a new scanning session is to be executed, the drive controller controls the drive unit to position the top plate and the detector unit at the relative position indicated by the stored relative position information.

PREFERRED EMBODIMENTS OF THE INVENTION

First Embodiment

An X-ray CT system as a first embodiment is described with reference to the drawings.

[Configuration]

Figure 1:
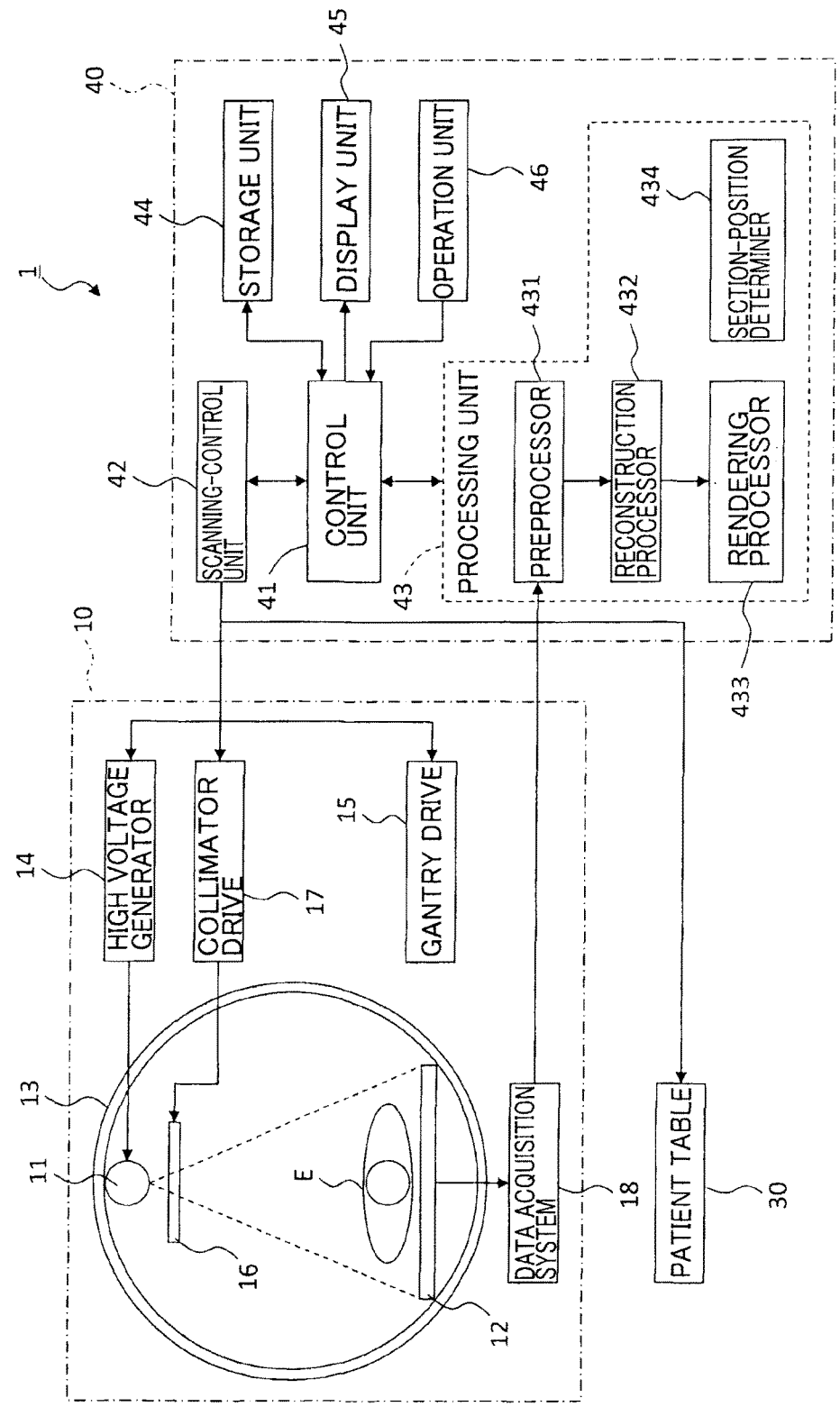
FIG. 1 is a block diagram of the configuration of an X-ray CT system as a first embodiment.
Figure 2:
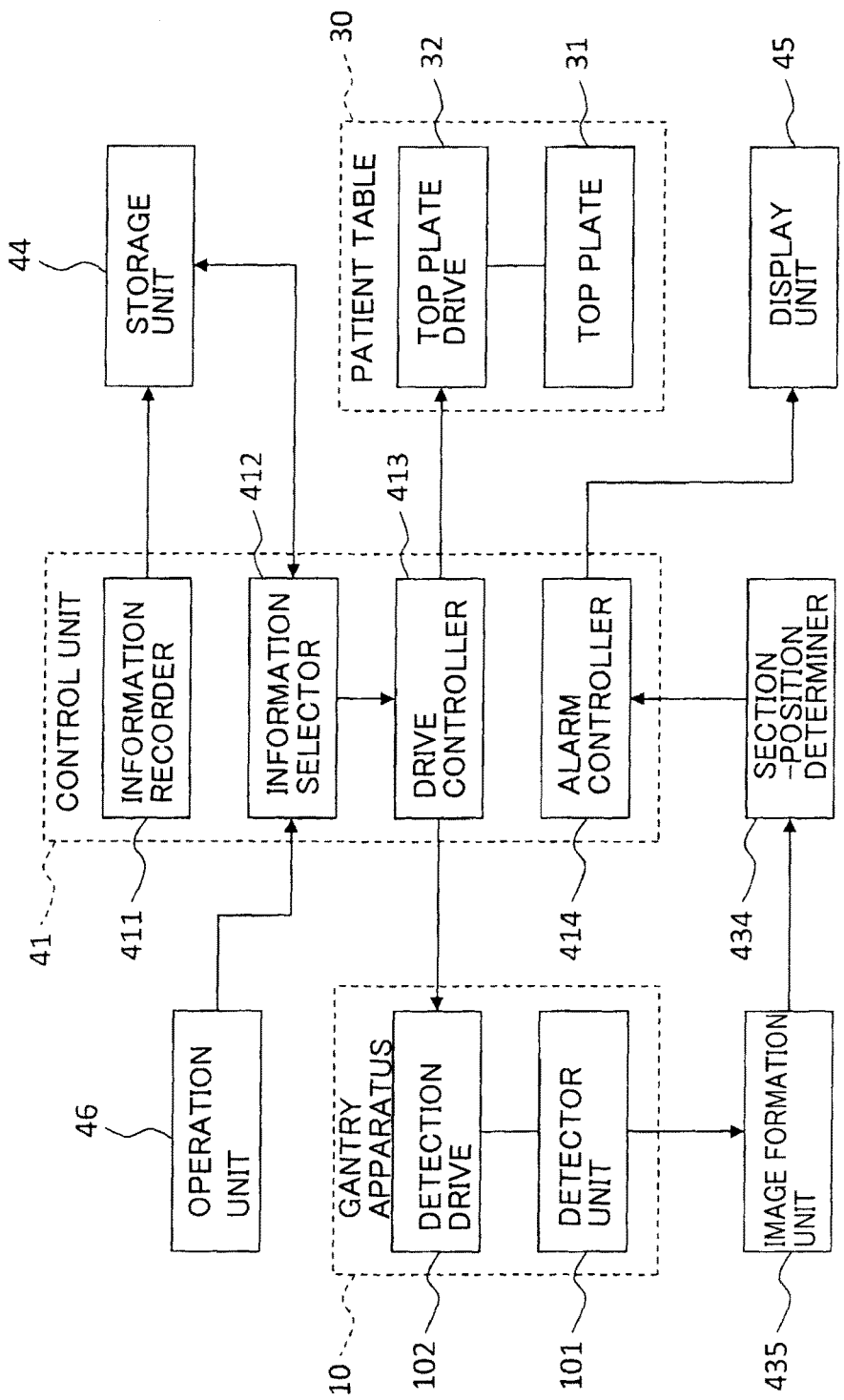
FIG. 2 is another block diagram of the configuration of the X-ray CT system as a first embodiment.

Referring to FIGS. 1 and 2, the configuration of an X-ray CT system 1 as a first embodiment is described only as an example. In the following description, the terms "image" and "image data" may be used interchangeably.

The X-ray CT system 1 is configured to include a gantry apparatus 10, a patient table 30, and a console device 40.

(Gantry Apparatus)

The gantry apparatus 10 is a piece of apparatus that radiates X-rays on a subject E and gathers data by detection of X-rays that have passed through the subject E. The gantry apparatus 10 comprises an X-ray generator 11, an X-ray detector 12, a rotating body 13, a high voltage generator 14, a gantry drive 15, an X-ray collimator 16, a collimator drive 17, and a data acquisition system 18.

The X-ray generator 11 is configured to include an X-ray tube for generating X-rays (for example, a vacuum tube generating a beam in circular cone or in pyramid-shape, not shown). The X-rays generated are directed to and radiated on the subject E.

The X-ray detector 12 is configured to include a plurality of X-ray detector elements (not shown). The X-ray detector 12 detects, with the X-ray detector elements, X-ray intensity distribution data (hereinafter, it may be also referred to as "detection data") that indicate the intensity distribution of the X-rays that have passed through the subject E, and the detector outputs detection data as signals in electric current.

The X-ray detector 12 comprises, for example, a two-dimensional X-ray detector (area detector) in which a plurality of detector elements are set in each of two inter-orthogonal directions (slicing direction and channeling direction). For example, X-ray detector elements are aligned in 320 lines in slicing direction. By using such an X-ray detector having detector elements in multi-line configuration, a three-dimensional region having a certain width in slicing direction can be scanned in one scanning rotation (volumetric scanning). By the way, the slicing direction corresponds to the rostrocaudal direction of the subject E while the channeling direction corresponds to the direction of rotation of the X-ray generator 11.

The detector unit 101 shown in FIG. 2 is an assembly for detecting X-rays and includes at least an X-ray generator 11 and an X-ray detector 12.

The rotating body 13 is a member that supports the X-ray generator 11 and the X-ray detector 12 to face each other in position, with the subject E between them. The rotating body 13 has a through-opening in the slicing direction, and into this opening, a top plate, on which the subject E is placed, is inserted. The rotating body 13 is rotated along a circular orbit around the subject E as the center of rotation by, the gantry drive 15 while the subject E is being scanned.

The gantry drive 15 has a mechanism that rotates the detector unit 101 for scanning and a mechanism that translates the detector unit 101. The latter mechanism is shown in FIG. 2 as a detection drive 102. The detection drive 102 makes the detector unit 101 move in translation and in slanting movement (tilting).

The translation is a displacement in an arbitrary direction. For example, the translation involves movements in one or more of up and down direction, right and left direction, and front and rear direction. Herein, the right and left direction is designated as the direction defined by the shorter side of the top plate 31, which is described later. In other words, it is the direction along the body width of the subject E placed on the top plate 31. The front and rear direction is designated as the direction defined by the longer side of the top plate 31. In other words, the front and rear direction is the rostrocaudal direction of the subject E placed on the top plate 31. The up and down direction is the direction perpendicular to both the right and left direction and the front and rear direction. If movement is possible in two or more of these three directions, then the detection drive 102 can move the detector unit 101 in a given direction by combining movements in these two or more directions.

The tilting is the action of changing the angle of inclination of the top plate 31 with respect to the detector unit 101. The angle of inclination can be defined as the angle, for example, between the normal of the upper surface of the top plate 31 and the normal of the plane where the detector unit 101 rotates during the scanning (i.e., the rotating plane of the rotating body 13).

The high voltage generator 14 supplies a high voltage to the X-ray generator 11, and at the high voltage, the X-ray generator 11 generates X-rays. The X-ray collimator 16 forms a slit (opening) by changing the size and shape of the slit, and thereby, adjusts the fan angle of the X-rays radiated by the X-ray generator 11 (i.e., the flare angle in the channeling direction) and the cone angle of the X-rays (i.e., the flare angle in the slicing direction). The collimator drive 17 drives the X-ray collimator 16 and modifies the size and shape of the slit.

The data acquisition system 18 (DAS: Data Acquisition System) gathers detection data from the X-ray detector 12 (from each of the X-ray detector elements). Furthermore, the data acquisition system 18 converts the detection data gathered (in current signals) into voltage signals, integrates them periodically for amplification and then converts them into digital signals. The data acquisition system 18 sends the detection data that have been converted into digital signals to the console device 40.

(Patient Table)

The top plate 31 of the patient table 30 (see FIG. 2) is where the subject E is placed lying. The patient table 30 is provided with a top plate drive 32 for moving the subject E placed on the top plate 31. The top plate drive 32 is capable of moving the top plate 31, for example, in the top and bottom direction, the right and left direction, and the front and rear direction as mentioned above. In addition, the top plate drive 32 may be configured to be capable of tilting the top plate 31.

The detection drive 102 and the top plate drive 32 are examples of "drive unit" that change the relative position between the top plate 31 and the detector unit 101. Although this embodiment comprises both the mechanism of moving the top plate 31 (first drive unit) and the mechanism of moving the detector unit 101 (second drive unit), it is possible to employ another configuration that comprises only one of these mechanisms.

(Console Device)

The console device 40 is used for operating the X-ray CT system 1 and for inputting information. In addition, the console device 40 reconstructs the detection data input from the gantry apparatus 10 into CT image data (tomographic data and volumetric data), which represent some internal morphology of the subject E. The console device 40 is configured to include a control unit 41, a scanning-control unit 42, a processing unit 43, a storage unit 44, a display unit 45 and an operation unit 46.

The control unit 41, the scanning-control unit 42 and the processing unit 43 are further configured to include, for example, processing units and storage devices. The processing units may be, for example, a CPU (Central Processing Unit), a GPU (Graphic Processing Unit), or an ASIC (Application Specific Integrated Circuit). The storage devices may include, for example, a ROM (Read Only Memory), a RAM (Random Access Memory), or an HDD (Hard Disc Drive). The storage devices store computer programs for execution of the functions of all parts of the X-ray CT system 1, and the processing units are for executing the computer programs, which realize the functions. The control unit 41 controls each part of the system. The internal configuration of the control unit 41, which is shown in FIG. 2, is described later.

The scanning-control unit 42 controls in unity the actions involved in the scanning with X-rays. The unified control here includes control of the high voltage generator 14, control of the gantry drive 15, control of the collimator drive 17, and control of the patient table 30. The control of the high voltage generator 14 is to control the high voltage generator 14 in such a way that it supplies a predetermined high voltage to the X-ray generator 11 at a predetermined timing. The control of the gantry drive 15 is to control the gantry drive 15 in such a way that it makes the rotating body 13 rotate at a predetermined velocity at a predetermined timing. The control of the collimator drive 17 is to control the collimator drive 17 in such a way that the X-ray collimator 16 forms a slit having a predetermined size and a predetermined shape. The control of the patient table 30 is to control the patient table 30 in such a way that it moves the top plate to a predetermined position at a predetermined timing. In volumetric scanning, the action of scanning is performed in the state that the position of the top plate is fixed. In helical scanning, the action of scanning is performed while the top plate is being moved.

The processing unit 43 executes various types of processing on the detection data coming from the gantry apparatus 10 (data acquisition system 18). The processing unit 43 is configured to include a preprocessor 431, a reconstruction processor 432, a rendering processor 433, and a section-position determiner 434.

The preprocessor 431 executes on the detection data, which have been received from the gantry apparatus 10, such preprocesses as logarithmic transformation, offset correction, sensitivity correction, and beam hardening correction, and the preprocessor thereby generates projection data.

The reconstruction processor 432 generates CT image data (tomographic data and volumetric data) based on the projection data, which have been generated by the preprocessor 431. As reconstruction-processing of tomographic data, such arbitrary methods as two-dimensional Fourier transformation and convolution back projection can be applied. Volumetric data are generated by interpolating sets of tomographic data, which have been reconstructed. As reconstruction-processing of volumetric data, such arbitrary methods as cone-beam reconstruction, multi-slice reconstruction, and magnified reconstruction can be applied. The volumetric scanning that uses the X-ray detector having its elements in multi-line arrangement as described above can reconstruct volumetric data that cover a wide range.

The rendering processor 433 is capable of executing, for example, MPR processing and volume rendering. The MPR processing is an image processing for generating MPR image data that represent an arbitrarily set section, by executing rendering on the volumetric data, which have been generated by the reconstruction processor 432, with respect to the set section. The volume rendering is an image processing for generating pseudo-three-dimensional image data that represent a three-dimensional region of the subject E, by sampling the volumetric data along an arbitrary eyeline (rays) and by adding the sampled values (CT values).

The image formation unit 435 shown in FIG. 2 includes a preprocessor 431, a reconstruction processor 432, and a rendering processor 433. The image formation unit 435 is an example of "formation unit" that forms image data of the subject E based on the data acquired by the scanning.

The section-position determiner 434 compares two sets of image data acquired during the scanning sessions executed at different timings, and determines whether the positions in the subject E sectionally depicted by these sets of image data are substantially identical or not. The section-position determiner 434 is a functional example of "determiner unit".

The following description is an example of processing that can be executed by the section-position determiner 434. If the sectional positions are substantially identical, then the two sets of image data are to present substantially identical images. The section-position determiner 434 calculates, for example, a differential image (subtraction image) from these two sets of image data, and determines whether this differential image describes nothing substantial or not. If the result of the determination is that the differential image describes nothing substantial, then the section-position determiner 434 decides that the sectional positions depicted by these sets of image data are substantially identical.

Another processing example may be that the section-position determiner 434 extracts data for feature parts (organs, blood vessels, etc.) from each set of image data, and determines whether the feature parts are substantially identical in shape and/or in position. If the result of the determination is that the feature parts are substantially identical in shape and/or position, the section-position determiner 434 decides that the sectional positions depicted by these sets of image data are substantially identical. The process for determining the oneness of sectional positions is not limited to these examples, and any imaging processing technique can be applied arbitrarily.

The expression that the sectional positions are "substantially identical" means not only a case where they are completely identical but also a case where predetermined allowable errors exist. Examples that allowable errors exist are a case where the number of pixels used for the image depicted by the above-mentioned differential image is less than a predetermined threshold value, a case where the margin of error relating to the shapes and/or positions of the above-mentioned feature parts is less than a predetermined threshold value, and a case where the margin of error relating to the position and direction of an object (e.g., a puncture needle) depicted with the subject E is less than a predetermined threshold value.

The storage 44 stores detection data, projection data, reconstruction-processed image data, etc. The display unit 45 comprises a displaying device, for example, an LCD (Liquid Crystal Display). The operation unit 46, which is used for input of various instructions and information to the X-ray CT system 1, comprises, for example, a key-board, a mouse, a track ball, a joystick, and a foot switch. In addition, the operation unit 46 may be configured to include the GUI (Graphical User Interface) that is used with the display unit 45.

Now, the control unit 41 is described with reference to FIG. 2. The control unit 41 comprises an information recorder 411, an information selector 412, a drive controller 413, and an alarm controller 414.

The information recorder 411 makes the storage unit 44 store relative position information that indicates the relative position between the top plate 31 and the detector unit 101, which position is applied for the scanning. The relative position information is acquired from the control contents of how the drive controller 413 controls the top plate drive 32 and the detection drive 102.

The following is a specific example of this processing. The drive controller 413 moves the top plate 31 by sending a control signal to the top plate drive 32, and the drive controller 413 moves the detector unit 101 by sending a control signal to the detection drive 102. These control signals include, as their control contents, information that indicates directions and amounts of movement. In addition, predetermined reference positions are respectively set for the movement of the objects, which are driven by the top plate drive 32 and the detection drive 102. The information recorder 411 has a reference position for the top plate 31 and a reference position for the detector unit 101 prerecorded as initial relative positions. The relative position is expressed, for example, as coordinates in a preset three-dimensional coordinate system. For example, the three-dimensional coordinate system expresses positions in a space where the gantry apparatus 10 and the patient table 30 are set up. Whenever the drive controller 413 transmits a control signal, it also sends the control content of the signal to the information recorder 411. The information recorder 411 records, respectively, the control contents that relate to the movement of the top plate 31 and the control contents that relate to the movement of the detector unit 101. In this way, the information recorder 411 can keep a control record for the movement of the top plate 31 and a control record for the movement of the detector unit 101. Each control record has a corresponding reference position as its starting point. By referring to these control records, the information recorder 411 can calculate the current positions of the top plate 31 and of the detector unit 101 as above-mentioned coordinates. During the scanning, the information recorder 411 calculates the respective coordinates of the top plate 31 and of the detector unit 101 in real time, and calculates the respective displacements from the coordinate changes, with the displacements defining the relative position between the top plate 31 and the detector unit 101. The information recorder 411 makes the storage unit 44 store the relative position information that indicates the relative position. The processing executed by the information recorder 411 is not restricted to this method, and another technique may be applied to calculate the relative position between the top plate 31 and the detector unit 101.

Now, the information selector 412 is described. After scanning is performed in several sessions, and the relative position information for two or more scanning sessions has been stored in the storage unit 44, the information selector 412 selects a piece of relative position information that corresponds to a particular scanning session out of the stored relative position information. The drive controller 413 controls the top plate drive 32 and/or the detection drive 102 in accordance with the relative position information selected by the information selector 412. The information selector 412 is a functional example of "selection unit". The following is an example of series of actions taken by the information selector 412.

The following actions are described as a first example. For the first exemplary actions, the selection unit includes a display unit 45 and an operation unit 46 in addition to the information selector 412. The display unit 45 displays two relative positions or more from the relative position information stored in the storage unit 44. These relative positions are shown, for example, as information in letters or information in images. Examples of the information in letters are identification information for each scanning session (for example, the name, number, etc. that are given to each scanning session, or the name of the organ targeted during each scanning session) and information indicating a relative position (e.g., the numerical value indicating the above-mentioned displacement, and the coordinates that indicates the positions of the top plate 31 and the detector unit 101). Examples of the information in images are an icon that indicates each scanning session, an icon that indicates the organ targeted during the scanning session, an icon that indicates the relative position, etc. From among the two or more relative positions displayed on the display unit 45, the user selects a desired relative position by using the operation unit 46. The information selector 412 reads out the relative position information that corresponds to the selected relative position from the storage unit 44. Furthermore, the information selector 412 calculates the directions and amounts of displacement for the movement of the top plate 31 and/or the detector unit 101 from the read-out relative position information and the respective current positions of the top plate 31 and the detector unit 101, in order to move the top plate 31 and/or the detector unit 101 from the current relative position as starting point to the relative position indicated by the relative position information. The calculation processing involves calculation of the displacement between the coordinates of the relative positions, for example, in the above-mentioned three-dimensional coordinate system. The information selector 412 sends the information indicating the calculated directions and amounts of displacement to the drive controller 413. The drive controller 413 generates control signals based on the information, which has been received from the information selector 412. The drive controller, then, sends the signals to the top plate drive 32 and/or the detection drive 102. The top plate drive 32 and/or the detection drive 102 move the top plate 31 and/or the detector unit 101 in accordance with the control signals. As a result, the top plate 31 and the detector unit 101 are set at the relative position indicated by the relative position information selected by the information selector 412.

Now, as a second example, a series of actions are described. For the second exemplary actions, the selection unit includes an operation unit 46 in addition to the information selector 412. For a specific scanning session, the user performs a predetermined operation by using the operation unit 46. The expression "for a specific scanning session" herein involves a predetermined operation before, during, or after the scanning session. "Before the scanning session" indicates an arbitrary timing between the last-performed scanning session and the scanning session to be performed now. In addition, if the scanning session to be performed this time is the first scanning session, the expression means literally "before this scanning session". "After the scanning session" indicates an arbitrary timing between this scanning session and the next scanning session. The information selector 412 attaches identification information to the relative position information stored in the storage unit 44 for the scanning session for which the predetermined operation has been performed. Here, the identification information is, for example, a flag. After this scanning session that is explained above, and before another scanning session to be performed (which may be also referred to as a "new scanning session"), the information selector 412 selectively reads out the relative position information for the scanning session for which the predetermined operation has been performed (i.e., the relative position information attached with identification information) from among the two or more pieces of relative position information stored in the storage unit 44. The processing actions that follow thereafter are similar to those of the first example. In this example, the relative position information to which identification information is attached can exist only as one piece of relative position information. If a piece of relative position information attached with identification information already exists when the above-mentioned predetermined operation is newly performed, then the information selector 412 deletes the existing identification information and attaches identification information to the relative position information that corresponds to this new, predetermined operation. By the way, it is also possible to make such an arrangement that identification information be attached to two or more pieces of relative position information. In that case, the configuration can display the relative positions indicated by two or more pieces of relative position information attached with identification information so that the user can select one of the relative positions in the same way as in the first example of actions.

Now, the alarm controller 414 is described. The alarm controller 414 makes an alarm if the result of determination by the section-position determiner 434 is that the sectional positions of the subject E depicted by two sets of image data are not substantially identical. The alarm controller 414 is a functional example of "alarm unit". An example of alarming processing displays predetermined alarming information on the display unit 45. The alarming information can be information in letters like a warning message or information in images indicating a warning. Also, this can be a predetermined warning window to be popped up. In these cases, the alarm unit includes a display unit 45 in addition to the alarm controller 414. In addition, a voice activator (not shown) may be controlled to sound a beep or a warning message. In this case, the alarm unit includes a voice activator in addition to the alarm controller 414.

[Actions]

Figure 3:
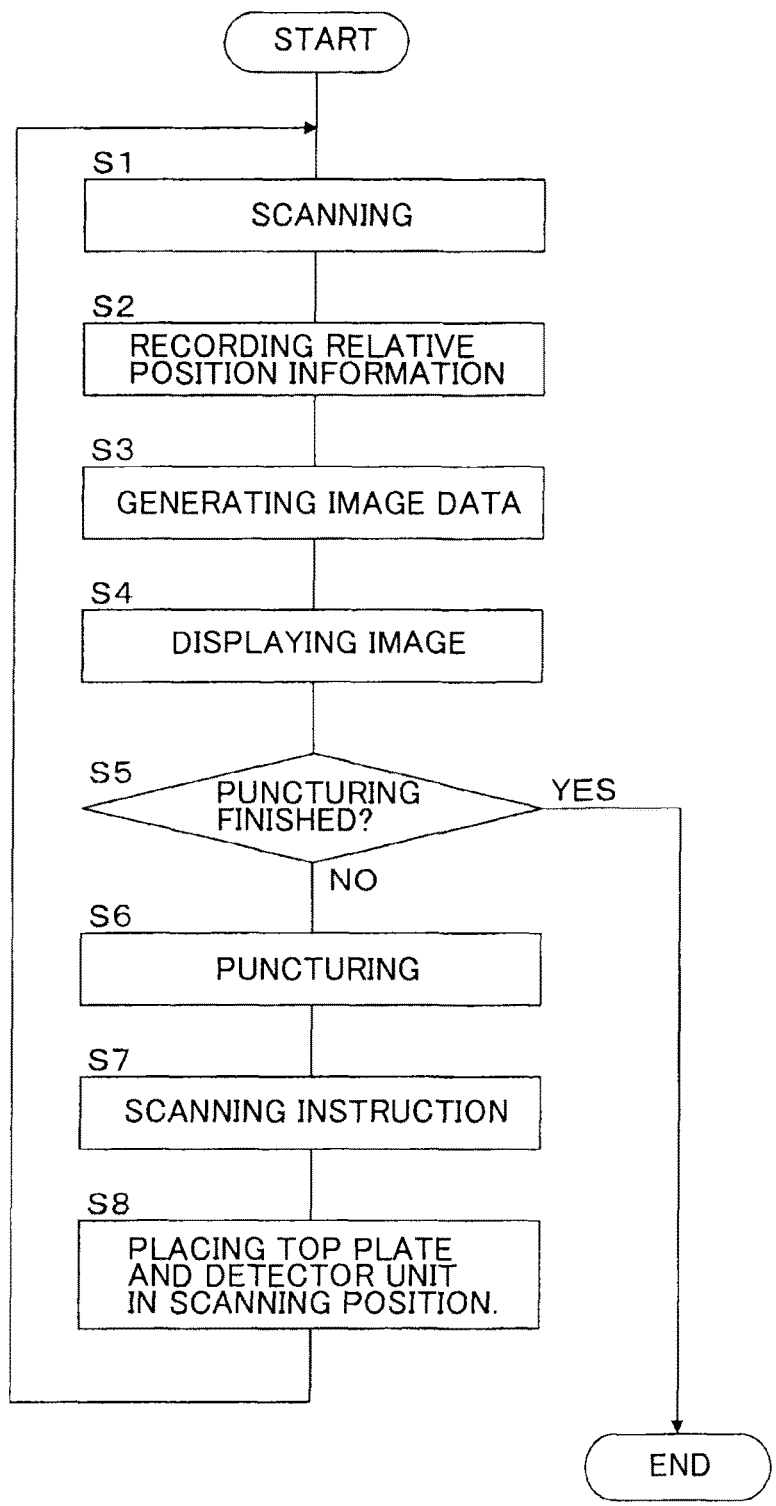
FIG. 3 is a flow chart showing exemplary actions of the X-ray CT system as a first embodiment.

Now, actions taken by the X-ray CT system 1 as an embodiment are described. The flow chart shown in FIG. 3 shows exemplary actions taken for a puncturing procedure.
(S1: Scanning is Performed.)

At first, a subject E is placed on the top plate 31 of the patient table 30 and is inserted into the opening of the gantry apparatus 10. When a predetermined scanning-starting operation is made, the control unit 41 sends a control signal to the scanning-control unit 42. The scanning-control unit 42, upon receiving this control signal, controls the high voltage generator 14, the gantry drive 15, and the collimator drive 17 for scanning the subject E with X-rays. The X-ray detector 12 detects X-rays that have passed through the subject E. The data acquisition system 18 gathers detection data sequentially generated by the X-ray detector 12 for the scanning. The data acquisition system 18 sends the gathered detection data to the preprocessor 431.
(S2: Relative Position Information is Recorded.)

The information recorder 411 makes the storage unit 44 store the relative position information used for the scanning at step 1 by performing, for example, one of the above-mentioned exemplary actions.
(S3: Image Data are Generated.)

The preprocessor 431 executes the above-mentioned preprocessing on the detection data coming from the data acquisition system 18 in order to generate projection data. The reconstruction processor 432 executes reconstruction-processing, in accordance with preset reconstruction conditions, on the projection data to generate volumetric data. The rendering processor 433 generates MPR image data based on the volumetric data. The MPR image data may be any image data for a three-orthogonal-axis image or image data for an oblique image that corresponds to an arbitrarily set section.
(S4: An Image is Displayed.)

The control unit 41 makes the display unit 45 display an image based on the image data generated at step 3.
(S5, S6: Puncturing is Performed.)

The medical specialist performs a predetermined operation to move and locate the top plate 31 and the gantry apparatus 10 relative to each other for placing the subject E at a predetermined puncturing operation position, and the specialist performs a puncturing operation on the subject E while referring to the image displayed at step 4. The puncturing performed with this embodiment is executed step by step with actions of scanning and puncturing being repeated one after the other.
(S7: Scanning is Instructed.)

Stopping the puncturing operation, the specialist executes a predetermined operation as instruction for starting another session of scanning.
(S8: The Top Plate and the Detector Unit are Placed in Scanning Position.)

The control unit 41 having received this scanning instruction moves the top plate 31 and/or the detector unit 101 in accordance with the relative position information stored at step 2 according to, for example, one of the exemplary actions previously described. By this movement, the top plate 31 and the detector unit 101 are located at the same relative position as during the scanning session at step 1. At this point, the flow of the procedure returns to step 1, and another session of scanning is performed. By the way, if the procedure is repeated from step 1, then the relative position information may be recorded at least once at step 2.

The above-mentioned part of the procedure is repeated until the completion of the puncturing (until "YES" at step 5).

Operation and Effects

Now, the operation and effects of the X-ray CT system 1 as an embodiment are described.

The X-ray CT system 1 comprises a patient table 30, a gantry apparatus 10, an image formation unit 435, a top plate drive 32 and/or a detection drive 102 (also collectively referred to as "drive unit"), a storage unit 44, and a drive controller 413. The patient table 30 has a top plate 31, on which a subject E is placed. The gantry apparatus 10 carries out scanning on the subject E by rotating the detector unit 101, which comprises an X-ray tube (X-ray generator 11) and an X-ray detector 12 set facing each other. The image formation unit 435 generates image data of the subject E based on the data acquired by the scanning. The drive unit changes the relative position between the top plate 31 and the detector unit 101. The storage unit 44 stores the relative position information that indicates the relative position applied for the scanning. For a new scanning session to be performed, the drive controller 413 controls the drive unit and places the top plate 31 and the detector unit 101 at the relative position indicated by the relative position information, which is stored in the storage unit 44.

With the X-ray CT system 1, when a new scanning session is to be performed, the relative position between the top plate 31 and the detector unit 101 of a past scanning session can be automatically reproduced. It is, therefore, possible to achieve simplification and time-saving in the work of placing a subject E in scanning position.

The above-mentioned relative position may arbitrarily include one or more of the following three factors: (1) a first relative position defined in the longitudinal direction (above-mentioned front and rear direction) of the top plate 31, (2) a second relative position defined in the lateral direction (above-mentioned right and left direction) of the top plate 31, and (3) a third relative position defined in the direction (above-mentioned up and down direction) perpendicular to both the first relative position and the second relative position. In addition, the above-mentioned relative position may also include the angle of inclination between the top plate 31 and the detector unit 101.

The X-ray CT system 1 may be configured to store the relative position information for one or more scanning sessions if the scanning is performed in multiple sessions. Furthermore, the X-ray CT system 1 may be configured to include a selection unit that selects, if the stored relative position information includes the information for two or more scanning sessions of the multiple-session scanning, one of the two or more pieces of relative position information that correspond to two or more scanning sessions. Then, the system makes the drive controller 413 control the drive unit in accordance with the selected relative position information. In this way, two or more pieces of relative position information can be stored, and later, a desired one of the relative positions can be reproduced.

The selection unit may comprise a display unit 45 and an operation unit 46. The display unit 45 displays two or more relative positions, which are indicated by their corresponding two or more pieces of relative position information. The operation unit 46 is used for selecting one of the two or more relative positions displayed. The drive controller 413 controls the drive unit in accordance with the relative position information that corresponds to the selected relative position. In this way, the user can selectively reproduce a desired one of the relative positions. Such examples are described below. For example, in a puncturing procedure for treating lung cancer, puncturing is performed for each of the tumors, individually. In this case, relative position information can be recorded for each of the tumors. Later when a puncturing operation is to be performed for a certain tumor, the scanning position that corresponds to this tumor can be automatically reproduced by selectively applying the relative position information that corresponds to the tumor.

The selection unit may include an operation unit 46. In a case where the above-mentioned predetermined operation has been made with the operation unit 46 for a specific scanning session, the selection unit selects the relative position information of the scanning session for which the predetermined operation has been made, from among the two or more pieces of relative position information stored in the storage unit 44 before a new scanning session is performed. The drive controller 413 controls the drive unit in accordance with the selected relative position information. In this way, the user, in anticipation of reproducing the scanning position in the future, can execute the predetermined operation for the current scanning. This operation may be considered as locking of the scanning position for a future scanning. In other words, the scanning position is automatically reproduced in the following scanning.

The X-ray CT system 1 may include a section-position determiner 434 and an alarm unit. The section-position determiner 434 compares image data generated based on data acquired during a past scanning session with image data generated based on data acquired during a new scanning session and determines whether the sectional positions in the subject E depicted by these two sets of image data are substantially identical or not. If the result of the determination by the section-position determiner 434 is that the sectional positions are not substantially identical, then the alarm unit makes an alarm. The alarm unit includes, for example, an alarm controller 414 and a display unit 45 (or a voice activator). Even if the scanning position is reproduced, the sectional image acquired may differ from that of the previous scanning session due to, for example, body movements of the subject E. It is possible that the image may not show the puncture needle or the punctured object appropriately. In such a case, the puncturing operation cannot be performed precisely and smoothly. The present configuration enables the X-ray CT system 1 to notify the medical specialist of the occurrence of such a situation.

Second Embodiment

An X-ray CT system as a second embodiment is described with reference to the drawings. This embodiment is a configuration that can achieve simplification and time-saving in the work of placing a subject E in operational position for performing a medical procedure on the subject E. The medical procedure herein means, for example, insertion of a puncture needle into the subject E with reference to an MPR image. By the way, no detailed description is given of the parts of the configuration that are the same as the first embodiment.

[Configuration]

Figure 4:
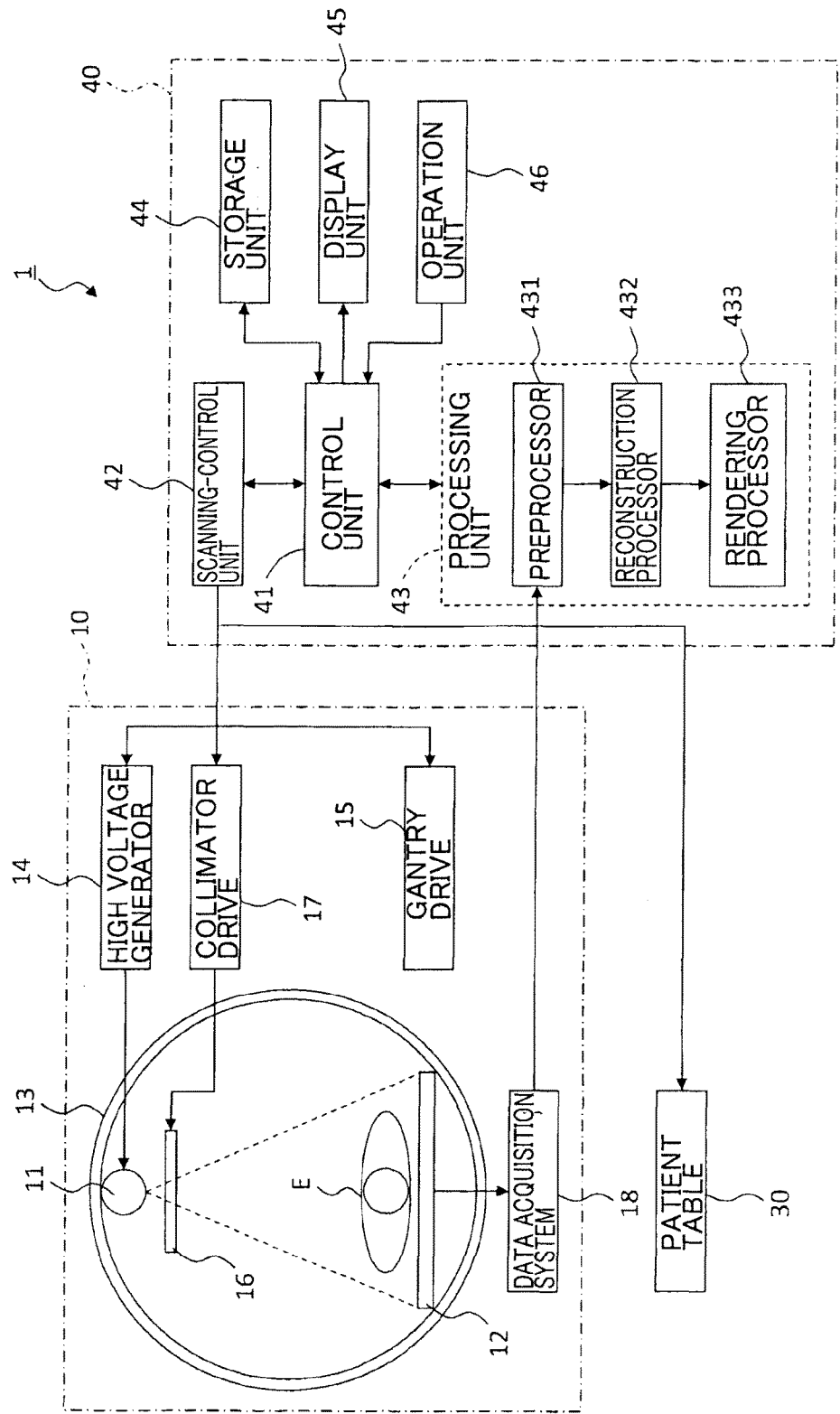
FIG. 4 is a block diagram of the configuration of an X-ray CT system as a second embodiment.
Figure 5:
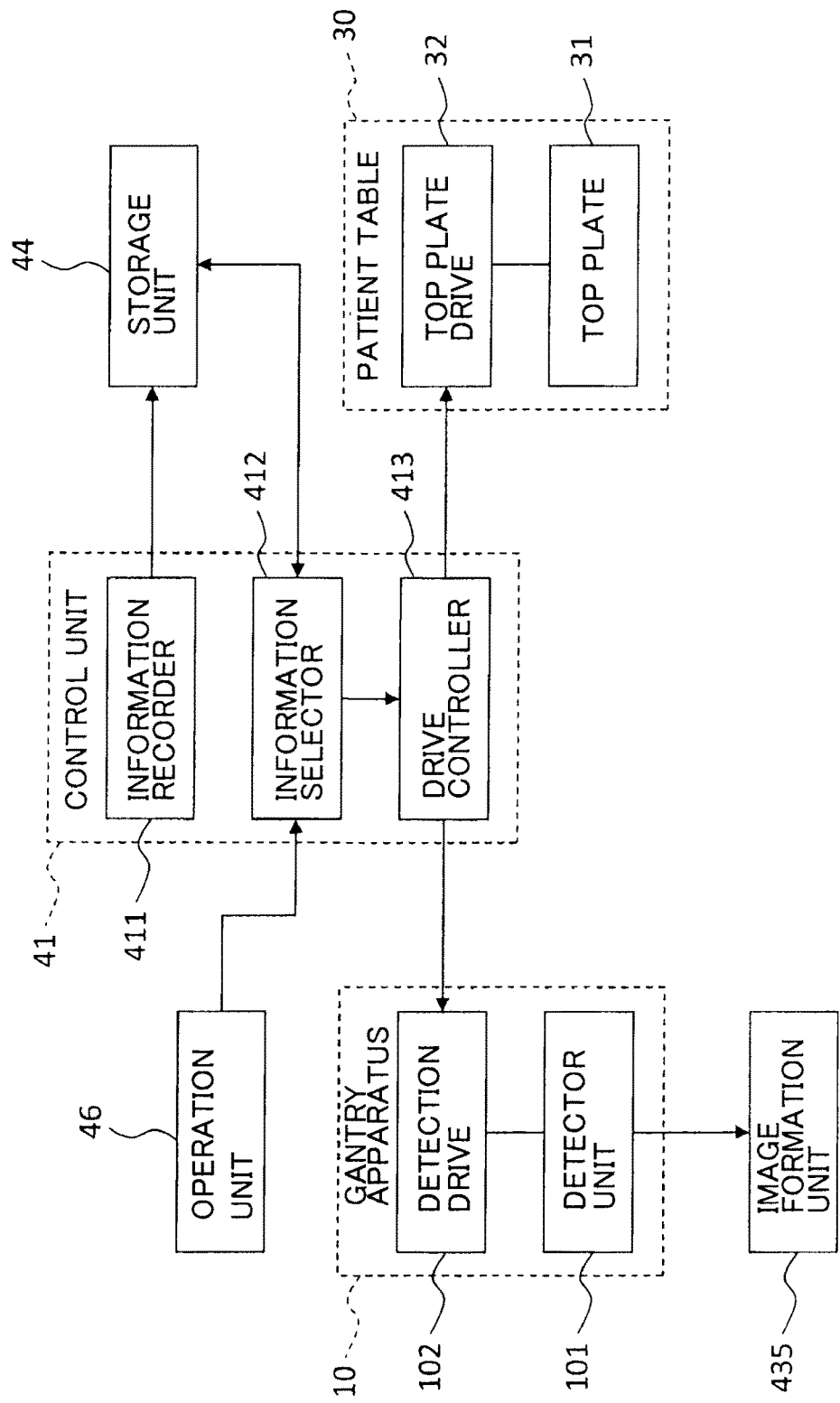
FIG. 5 is another block diagram of the configuration of the X-ray CT system as a second embodiment.

Referring to FIGS. 4 and 5, the exemplary configuration of the X-ray CT system 1 is described as a second embodiment.

The processing unit 43 as this embodiment is configured to include a preprocessor 431, a reconstruction processor 432, and a rendering processor 433.

Likewise, the control unit 41 comprises an information recorder 411, an information selector 412, and a drive controller 413.

The information recorder 411 makes the storage unit 44 store the relative position information that indicates the relative position between the top plate 31 and the detector unit 101 at the time of the execution of a medical procedure on the subject E. The relative position information is acquired, for example, from the control contents of how the drive controller 413 controls the top plate drive 32 and the detection drive 102.

When the top plate 31 (subject E) is at the position where the medical procedure is performed, the information recorder 411 calculates, in real time, the coordinates for each of the top plate 31 and the detector unit 101 in response to an instruction input, for example, from the operation unit 46, and calculates the displacement between the two sets of coordinates. The displacement here defines the relative position between the top plate 31 and the detector unit 101. The information recorder 411 makes the storage unit 44 store the relative position information that indicates the relative position.

By the way, the relative position information can be values that the user sets in advance (e.g., 600 mm, which is the distance of the top plate 31 from the detector unit 101), or the relative position information can be the positional information of the top plate 31 and the detector unit 101 used for the puncturing operation performed at the same part of the same subject in the past, or the positional information of the top plate 31 and the detector unit 101 set as initial position in the operating room where the X-ray CT system 1 is installed. In these cases, there is no need for the information recorder 411 to calculate the displacement between the two sets of coordinates of the top plate 31 and the detector unit 101.

Now, the information selector 412 is described. If the medical procedure on the subject E is performed in a plurality of sessions, and the relative position information for two or more sessions of the medical procedure is stored in the storage unit 44, the information selector 412 selects one piece of relative position information that corresponds to one session. The drive controller 413 controls the top plate drive 32 and/or the detection drive 102 in accordance with the relative position information selected by the information selector 412. The actions of the information selector 412 in this embodiment can be described as first exemplary actions and second exemplary actions in the same way as in the first embodiment. Here, since the first exemplary actions are the same as in the first embodiment, no description is given of these actions.

The second exemplary actions of this embodiment are as follows. The selection unit includes an operation unit 46 in addition to the information selector 412 for execution of the second exemplary actions. The user performs a predetermined operation for a specific medical procedure by using the operation unit 46. The expression "for a specific medical procedure" herein means that a predetermined operation is performed before the medical procedure, during the medical procedure, or after the medical procedure. "Before the medical procedure" is an arbitrary timing between the last medical procedure and the medical procedure to be performed this time. If the medical procedure to be performed is a first medical procedure, then "before the medical procedure" literally means before this medical procedure.

"After the medical procedure" is an arbitrary timing between this medical procedure and the next medical procedure. The information selector 412 attaches identification information to the relative position information that is stored in the storage unit 44 for the medical procedure for which the predetermined operation has been performed. This identification information is, for example, a flag. After this medical procedure, and before another medical procedure (referred to also as "new medical procedure") is performed, the information selector 412 selectively reads out the relative position information of the medical procedure for which the predetermined operation has been performed (i.e., the relative position information attached with the identification information) from among the two or more pieces of relative position information stored in the storage unit 44. The actions that follow thereafter are the same as the first exemplary actions (refer to the first embodiment). Here, in this example, only one piece of relative position information attached with identification information can exist. If the relative position information attached with identification information already exists, and if the above-mentioned predetermined operation is newly performed, then the information selector 412 deletes the identification information that has been attached, and attaches identification information to the relative position information that corresponds to this new execution of the predetermined operation. By the way, it is also possible to make such an arrangement that two or more pieces of relative position information be attached with identification information. In that case, the configuration should include showing of two or more relative positions indicated by the relative position information attached with identification information, so that the user can select them in the same way as the first exemplary actions.

[Actions]

Figure 6:
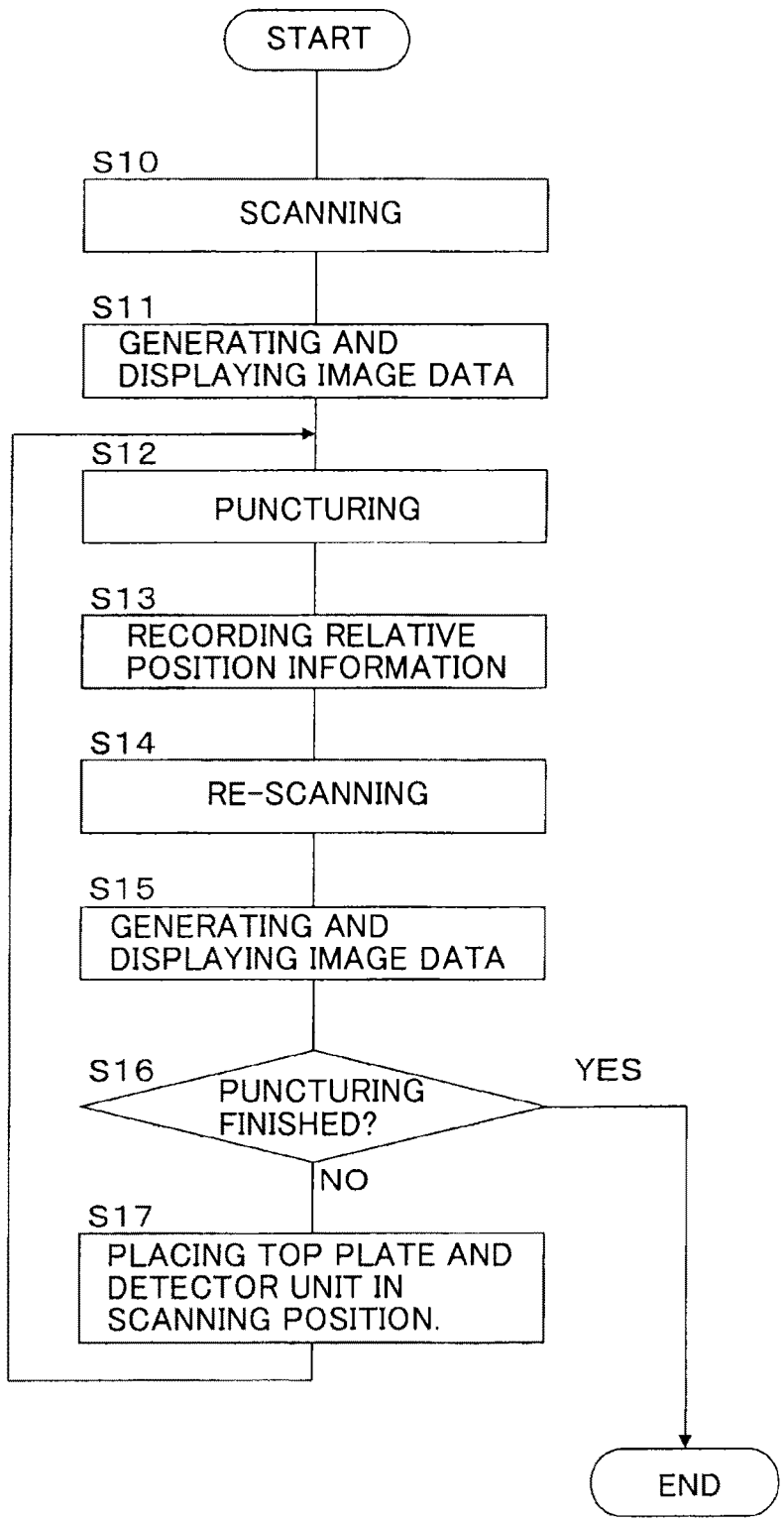
FIG. 6 is a flow chart showing exemplary actions of the X-ray CT system as a second embodiment.

Now, the actions of the X-ray CT system 1 as this embodiment are described. The flow chart shown in FIG. 6 shows exemplary actions for a case where a puncture is performed as a medical procedure.

(S10: Scanning is Performed.)

At first, the subject E is placed on the top plate 31 of the patient table 30 and is inserted into the opening of the gantry apparatus 10. When a predetermined scanning-starting operation is made, the control unit 41 sends control signals to the scanning-control unit 42. The scanning-control unit 42, upon receiving the control signals, controls the high voltage generator 14, the gantry drive 15, and the collimator drive 17 for scanning the subject E with X-rays. The X-ray detector 12 detects X-rays that have passed through the subject E. The data acquisition system 18 gathers detection data generated by the X-ray detector 12 during the scanning and sends the gathered detection data to the preprocessor 431.

(S11: Image Data are Generated and Displayed.)

The preprocessor 431 executes the above-described preprocessing on the detection data coming from the data acquisition system 18 and thereby generates projection data. The reconstruction processor 432 executes reconstruction-processing on the projection data in accordance with preset reconstruction conditions, and thereby, generates volumetric data. The rendering processor 433 generates MPR image data based on the volumetric data. The control unit 41 makes the display unit 45 display an image based on the generated MPR image data.

(S12: Puncturing is Performed.)

The medical specialist performs a predetermined operation to relatively move the gantry apparatus 10 and the top plate 31 in order to place the subject E at a predetermined puncturing operation position (i.e., a position where the medical procedure is performed). Then, the specialist performs puncturing on the subject E while referring to the image displayed at step 11. The puncturing performed for this embodiment is executed step by step with actions of scanning and puncturing being repeated one after the other. By the way, when the gantry apparatus 10 and the top plate 31 are moved relatively at step 12, it is possible to make the control unit 41 move the top plate 31 and/or the detector unit 101 in accordance with the relative position information stored in advance.

(S13: Relative Position Information is Recorded.)

The information recorder 411 stores the relative position information that indicates the relative position where the medical procedure is performed at step 12 in the storage unit 44 by performing, for example, one of the previously described exemplary actions.

(S14: Another Scanning Session is Executed.)

Stopping the puncturing operation, the specialist performs a predetermined operation for instructing another session of scanning. The control unit 41, upon receiving the scanning instruction, moves the top plate 31 and/or the detector unit 101 to the scanning position and performs a second scanning session.

(S15: Image Data are Generated and Displayed.)

Then, the control unit 41 makes the display unit 45 display another image based on the detection data generated during the second scanning session.

(S16: The Completion of the Puncture is Determined.)

With reference to the image displayed at step 15, the specialist determines whether or not the puncture needle has reached the object to be punctured. If the puncture needle has not reached the object (i.e., the puncturing has not been completed, or the "NO" results at step 16), then further puncturing is necessary. In this case, it is necessary to move the subject E to the puncturing operation position again. As a response, for example, the operator, who is not the medical specialist, instructs the operation unit 46 to move the top plate 31 and/or the detector unit 101. The operator can enter instructions with the console device 40, which is located outside the operating room, where the X-ray CT system 1 is installed. For example, the operator may make an instruction input by clicking the icon "Move Out" displayed on the display unit 45. If the top plate 31 is operated in this way from outside the operating room, it is not necessary for the medical specialist himself to make an input operation for instructing movements of the gantry apparatus 10. This arrangement is better on hygienic aspect. On the other hand, if a foot switch is provided as operation unit 46, then the specialist himself can perform the required instruction input while hygienic consideration is still maintained.

(S17: The Top Plate and the Detector Unit are Moved to the Puncturing Operation Position (i.e., the Position where the Medical Procedure is Performed).)

The control unit 41, which has received the instruction input at step 16, moves the top plate 31 and/or the detector unit 101 in accordance with the relative position information stored at step 13, according to, for example, one of the exemplary actions previously described. In this way, the top plate 31 and the detector unit 101 are placed at the same relative position as during the puncturing operation at step 12 (i.e., the subject E is placed at the puncturing operation position). The specialist performs puncturing in this state (step 12). By the way, if steps 17-12 are repeated, then the relative position information may be recorded at least once at step 13.

The above-mentioned procedure is repeated until the completion of the puncture (until the "YES" results at step 16).

Operation and Effects

Now, the operation and effects of the X-ray CT system 1 as this embodiment are described.

The X-ray CT system 1 comprises a patient table 30, a gantry apparatus 10, an image formation unit 435, a top plate drive 32 and/or a detection drive 102 (also collectively called "drive unit"), a storage unit 44, and a drive controller 413. The patient table 30 has a top plate 31, on which a subject E is placed. The gantry apparatus 10 scans the subject E by rotating the detector unit 101, which comprises an X-ray tube (X-ray generator 11) and an X-ray detector 12 set facing each other. The image formation unit 435 generates image data of the subject E based on the data acquired during the scanning. The drive unit changes the relative position between the top plate 31 and the detector unit 101. The storage unit 44 stores the relative position information that indicates the relative position where a medical procedure is performed on the subject E. When a new medical procedure is to be performed on the subject E, the drive controller 413 controls the drive unit to move the top plate 31 and the detector unit 101 to the relative position indicated by the relative position information stored in the storage unit 44.

When a new medical procedure is to be performed, the X-ray CT system 1 can automatically reproduce the relative position between the top plate 31 and the detector unit 101 that was applied for the medical procedure performed in the past (or the relative position set in advance). It is, therefore, possible to achieve simplification and time-saving in the work of placing the subject E at the position where the medical procedure is performed.

For a case where a medical procedure on the subject E is performed in a plurality of sessions, the X-ray CT system 1 may be configured to store relative position information for one or more sessions of the medical procedure. Furthermore, if the X-ray CT system 1 stores relative position information for two or more sessions of the medical procedure, which is performed in multiple sessions, the system may be configured to include a selection unit for selecting one of the two or more pieces of relative position information, so that the drive controller 413 controls the drive unit in accordance with the selected relative position information. In this way, two or more pieces of relative position information can be stored, and a desired one of the relative positions can be reproduced.

The selection unit may comprise a display unit 45 and an operation unit 46. The display unit 45 displays two or more relative positions indicated by the corresponding two or more pieces of relative position information. The operation unit 46 is used to select one of the two or more relative positions displayed. The drive controller 413 controls the drive unit in accordance with the relative position information that corresponds to the selected relative position. In this way, the user can selectively reproduce a desired one of the relative positions. Such examples are described below. In a puncturing operation for treating lung cancer, puncturing is performed individually for each of a plurality of tumors. In this case, relative position information can be recorded for each of the tumors. Later when a puncturing operation is performed for a certain tumor, by selectively applying the relative position information that corresponds to the tumor, the position where the medical procedure is performed for the tumor can be reproduced automatically.

The selection unit may include an operation unit 46. In a case where the above-mentioned predetermined operation has been executed with the operation unit 46 for a specific medical procedure on the subject E, the selection unit selects the relative position information of the medical procedure for which the predetermined operation has been performed, from among two or more pieces of relative position information stored in the storage unit 44 before a new medical procedure is to be performed on the subject E. The drive controller 413 controls the drive unit in accordance with the selected relative position information. In this way, if the user wants to reproduce, in the future, the position where the medical procedure has been performed, he or she can execute the predetermined operation for this specific position. This operation may be considered as locking of the position for a future medical procedure. In other words, in a future medical procedure, the position where the medical procedure is to be performed will be automatically reproduced.

Variant Embodiment from the First and Second Embodiments

The X-ray CT system 1 may be configured to include both the first embodiment and the second embodiment.

In other words, the storage unit 44 according to this variant embodiment stores the information that indicates the relative position applied for the scanning and the information that indicates the relative position applied for the medical procedure on the subject E as relative position information.

When a new scanning session is to be executed, the drive controller 413 controls the drive unit to place the top plate 31 and the detector unit 101 at the relative position applied for the scanning, the position being indicated by the stored relative position information. Furthermore, when a new medical procedure is to be performed on the subject E, the drive controller 413 controls the drive unit to place the top plate 31 and the detector unit 101 at the relative position applied for the medical procedure on the subject E, the position being indicated by the stored relative position information.

[Actions]

Figure 7:
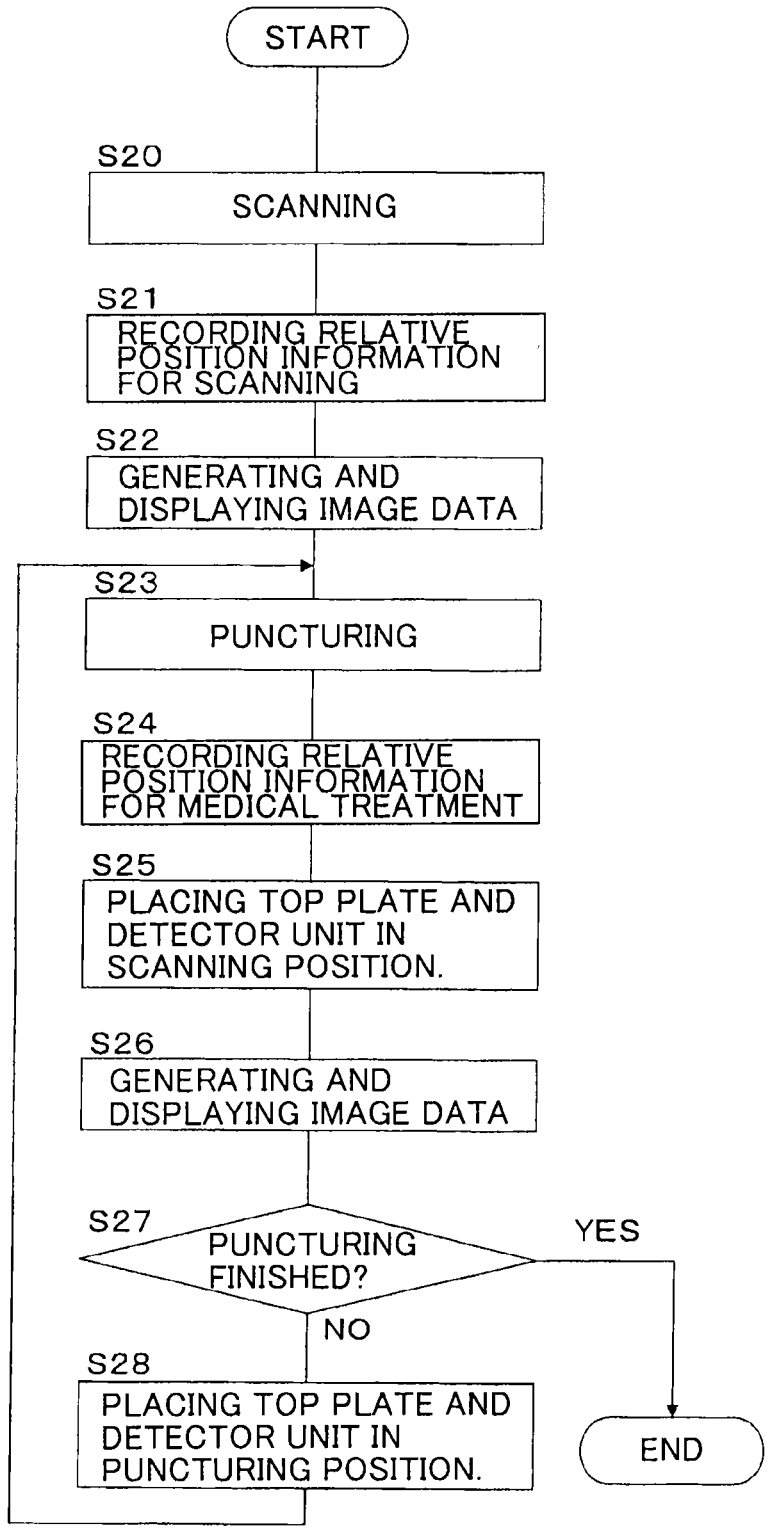
FIG. 7 is a flow chart showing exemplary actions of an X-ray CT system as a variant embodiment of the first and second embodiments.

Now, the actions of the X-ray CT system 1 as this variant embodiment are described. The flow chart shown in FIG. 7 shows exemplary actions for performing puncturing as a medical procedure.

(S20: Scanning is Performed.)

At first, the subject E is placed on the top plate 31 of the patient table 30 and is inserted into the opening of the gantry apparatus 10. When a predetermined scanning-starting operation is made, the control unit 41 sends control signals to scanning-control unit 42. The scanning-control unit 42, upon receiving the control signals, controls the high voltage generator 14, the gantry drive 15, and the collimator drive 17 for scanning the subject E with X-rays. The X-ray detector 12 detects X-rays that have passed through the subject E. The data acquisition system 18 gathers detection data generated by the X-ray detector 12 during the scanning and sends the gathered detection data to the preprocessor 431.

(S21: Relative Position Information for the Scanning is Recorded.)

The information recorder 411 makes the storage unit 44 store the information that indicates the relative position applied for the scanning at step 20 as relative position information by, for example, executing one of the exemplary actions mentioned for the first embodiment.

(S22: Image Data are Generated and Displayed.)

The preprocessor 431 performs preprocessing on the detection data coming from the data acquisition system 18 and thereby generates projection data. The reconstruction processor 432 generates volumetric data by executing reconstruction-processing on the projection data in accordance with preset reconstruction conditions. The rendering processor 433 generates MPR image data based on the volumetric data. The control unit 41 makes the display unit 45 display an image based on the generated MPR image data.

(S23: A Puncturing Operation is Performed.)

The medical specialist performs a predetermined operation for relatively moving the gantry apparatus 10 and the top plate 31, in order to move the subject E to a predetermined puncturing operation position (i.e., a position where the medical procedure is to be performed). Then, the specialist performs a puncturing operation on the subject E while referring to the image displayed at step 22. The puncturing performed for this embodiment is executed step by step with actions of scanning and puncturing being repeated one after the other.

(S24: Relative Position Information for the Medical Procedure is Recorded.)

The information recorder 411 makes the storage unit 44 store the information that indicates the relative position applied for the medical procedure performed at step 23 as relative position information by, for example, performing one of the previously described exemplary actions.

(S25: The Top Plate and the Detector Unit are Moved to the Scanning Position.)

After the puncturing has proceeded to a certain extent, the medical specialist executes a predetermined operation as instruction for starting another session of scanning. The control unit 41, upon receiving the scanning instruction, moves the top plate 31 and/or the detector unit 101 in accordance with the relative position information stored at step 21, according to, for example, one of the exemplary actions mentioned for the first embodiment. As a result, the top plate 31 and the detector unit 101 are placed at the same relative position as during the scanning at step 1. The X-ray CT system 1 executes a second scanning session in this state.

(S26: Image Data are Generated and Displayed.)

The control unit 41 makes the display unit 45 display an image based on the detection data generated for the second scanning.

(S27: The Completion of the Puncture is Determined.)

With reference to the displayed image at step 26, the medical specialist determines whether or not the puncture needle has reached the object to be punctured. If the puncture needle has not reached the object (i.e., the puncturing is not complete, and the "NO" results at step 27), then further puncturing is necessary. In this case, the medical specialist (or the operator) instructs, for example, with the operation unit 46, the system to move the top plate 31 and/or the detector unit 101.

(S28: The Top Plate and the Detector Unit are Moved to the Puncturing Operation Position (i.e., the Position where the Medical Procedure is Performed).)

The control unit 41, upon receiving the instruction input at step 27, moves the top plate 31 and/or the detector unit 101 in accordance with the relative position information stored at step 24, according to, for example, one of the exemplary actions mentioned for the second embodiment. As a result, the top plate 31 and the detector unit 101 are placed at the same relative position as during the puncturing operation at step 23 (the subject E is placed at the puncturing operation position). The medical specialist performs puncturing in this state (step 23).

The above-mentioned steps of the procedure are repeated until the completion of the puncture (until "YES" at step 27).

According to the X-ray CT system 1 as this variant embodiment, when a new scanning session is to be executed, the relative position between the top plate 31 and the detector unit 101 applied for a scanning session performed in the past can be automatically reproduced. Furthermore, according to the X-ray CT system 1 as this variant embodiment, when a new medical procedure is to be performed, the relative position between the top plate 31 and the detector unit 101 applied for a medical procedure performed in the past can be automatically reproduced. It is, therefore, possible to achieve simplification and time-saving in the work of setting the subject E in scanning position and in a position where a medical procedure is performed.

By the way, it is possible to arbitrarily set the sequence of moving the top plate 31 and/or the detector unit 101 between the scanning position and the puncturing operation position. For example, in a case where the position to be punctured on the subject E is clearly understood in advance, the X-ray CT system 1, at first, drives the top plate 31 and/or the detector unit 101 to place the subject E at the puncturing operation position, which is in the order that is the reverse of the variant embodiment just mentioned. In this case, predetermined values or the like can be used as relative position information that corresponds to the puncturing operation position. It is also possible that after the puncturing has proceeded to a certain extent, the X-ray CT system 1 drives the top plate 31 and/or the detector unit 101 to set the subject E in scanning position.

Third Embodiment

X-ray CT systems are sometimes used for scanning a specific region of the subject for a particular movement (e.g., beating of the heart, breathing, etc.). In the scanning of this type, careful consideration is given to how contents in X-ray CT image are influenced by such a particular movement. For example, the stomach or the lung tends to grow in amplitude in its motion being affected by the breathing of the subject. In a case where the X-ray CT image is aimed to show such a region, without any consideration of the influence by a particular movement, the shape and size of the region in image can change greatly depending on the timing of the execution of scanning. In such a situation, in image, the region including the object under observation is displayed different at every time phase, and this may make observation difficult.

To clear such a problem, there is a suggestion that the X-ray CT system generate an X-ray CT image in synchronization with a particular movement (e.g., the beating of the heart or the breathing). In this type of X-ray CT system, while the subject is being scanned repeatedly, gathered data are stored in relation to a biomedical signal received through an external device. The external device here is a device for acquiring a biomedical signal or information that represents a particular movement (e.g., a device for acquiring respiration waves, an electrocardiograph, etc.).

For image generation, the X-ray CT system can take into account cycles and phases of biomedical signals or the like. For example, when the X-ray CT system generates images, the user can select a particular phase in the cycle of a biomedical signal, based on the stored data of the biomedical signal, and the X-ray CT system executes reconstruction-processing on the data that correspond to the selected phase from among the data gathered over a period of time. For generating an image of a region whose particular movement is relatively large in amplitude, such a method of reconstruction-processing works to have the shape and size of the region displayed uniformly.

In a case where the X-ray CT image is being displayed in real time, however, if the reconstruction-processing is executed after the selection of a particular phase by the user referring to a biomedical signal (e.g., respiration waveform), then the real-time nature of the image display may be spoiled. In addition, it is difficult or complicated for the user to perform the operation of selecting a particular time phase in the cycle of a biomedical signal.

For example, in a case where the user is to perform such a medical procedure as ablation, biopsy, or drainage while referring to the X-ray CT image, if the real-time nature of the image is spoiled, then the execution of any of these procedures may be affected. In addition, since the user must select a particular phase while performing the procedure, the operation is difficult or complicated.

It is the object of the present embodiment to provide an X-ray CT system that is capable of uniformly displaying the shape and size of a targeted region in fluoroscopy while the shape and size of the region being scanned are changing under the breathing of the subject, with the system not requiring any complicated operation.

Figure 8:
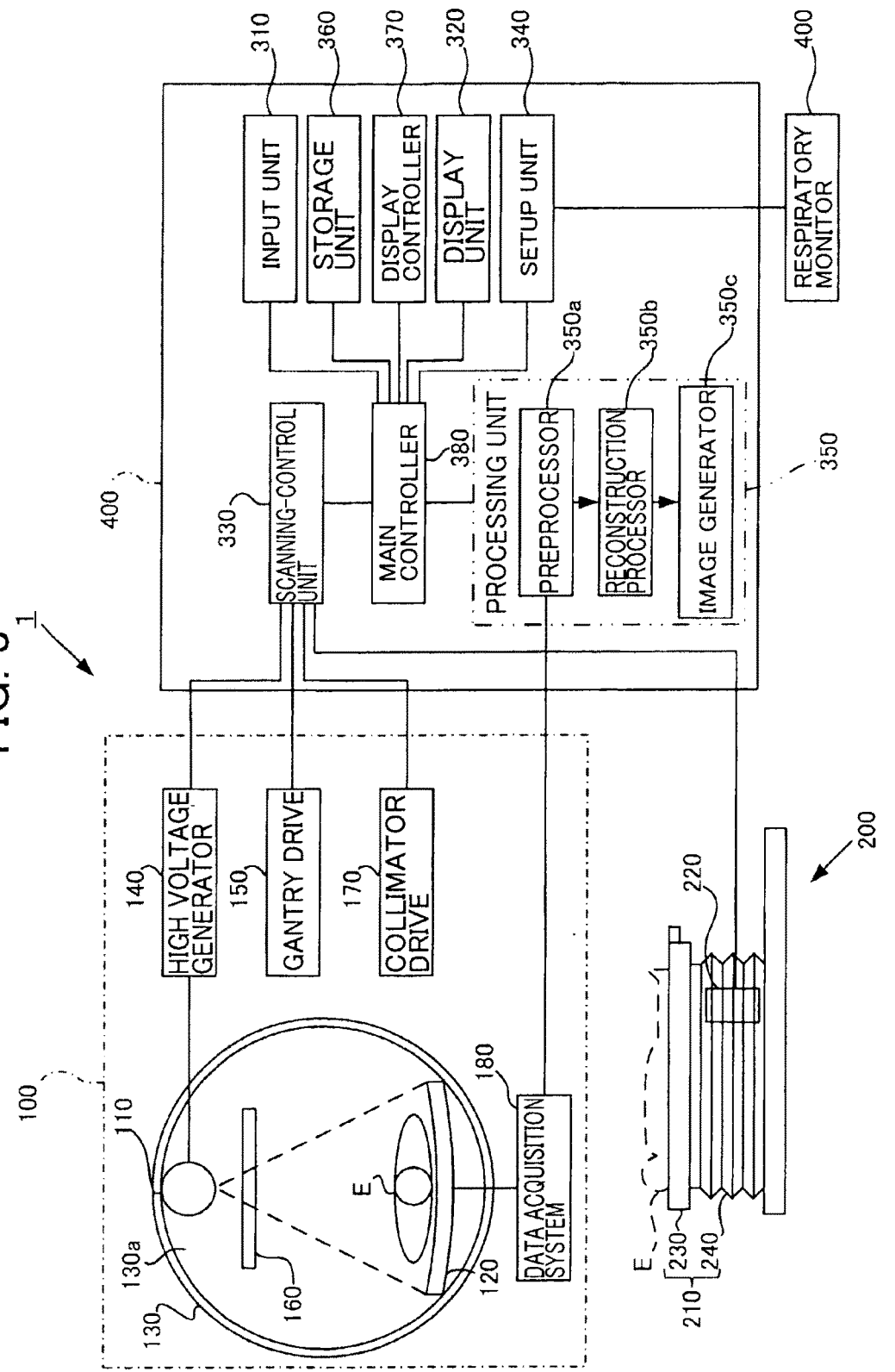
FIG. 8 is a block diagram showing an X-ray CT system as a third embodiment.

Now, the configuration of an X-ray CT system 1 as a third embodiment is described with reference to FIG. 8-FIG. 12. FIG. 8 is a block diagram showing the X-ray CT system as a third embodiment. By the way, the terms "image" and "image data" herein correspond with each other, and therefore, they may be used as identical terms for this embodiment.

[System Configuration]

As shown in FIG. 8, the X-ray CT system 1 is configured to include a gantry apparatus 100, a patient table 200 and a console device 300.

(Gantry Apparatus)

The gantry apparatus 100 is a piece of equipment that irradiates the subject E with X-rays and gathers detection data of X-rays that have passed through the subject E. The gantry apparatus 100 comprises an X-ray generator 110, an X-ray detector 120, a rotating body 130, a high voltage generator 140, a gantry drive 170, an X-ray collimator 160, a collimator drive 150, and a data acquisition system 180.

The X-ray generator 110 is configured to include an X-ray tube, which generates X-rays (for example, a vacuum tube that generates beams in circular cone or in pyramid-shape, not shown). The X-rays being generated are used for irradiating the subject E. The X-ray detector 120 is configured to include a plurality of X-ray detector elements (not shown). The X-ray detector 120 detects, with the X-ray detector elements, X-ray intensity distribution data (detection data), which shows the intensity distribution of X-rays that have passed through the subject E, and outputs the detection data as current signals. The X-ray detector 120 comprises a two-dimensional X-ray detector (area detector), which is, for example, an array of detector elements aligned in two inter-orthogonal directions (slicing direction and channeling direction). For example, X-ray detector elements are aligned in 320 lines in slicing direction. By using such an X-ray detector having a multi-line configuration, a three-dimensional region can be scanned with a relatively wide width in slicing direction for a scanning rotation (volumetric scanning). By the way, the slicing direction corresponds with the rostrocaudal direction of the subject E, and the channeling direction corresponds with the direction of rotation of the X-ray generator 110. It is not necessary, however, to use an X-ray detector of multi-line configuration like the one mentioned above for the X-ray detector 120 of this embodiment.

The rotating body 130 is a member that supports the X-ray generator 110 and the X-ray detector 120 facing each other, with the subject E being between them. The rotating body 130 has a through-opening 130a in the slicing direction and is configured to rotate around the subject E as its center, along a circular orbit in the gantry apparatus 100.

The high voltage generator 140 provides a high voltage to the X-ray generator 110, and the X-ray generator 110 at the high voltage generates X-rays. The gantry drive 170 drives the rotating body 130 to rotate. The X-ray collimator 160 has a slit (opening) having a predetermined width, and adjusts the X-ray fan angle (flare angle in the channeling direction) and the X-ray cone angle (flare angle in the slicing direction) of the X-rays radiated from the X-ray generator 110 by changing the width of the slit. The collimator drive 150 drives the X-ray collimator 160 so that X-rays generated by the X-ray generator 110 are formed in a predetermined shape.

The data acquisition system 180 (DAS) gathers detection data generated by the X-ray detector 120 (i.e., by each of the X-ray detector elements). In addition, the data acquisition system 180 converts the gathered detection data (current signals) into voltage signals, periodically integrates the voltage signals for amplification, and then converts them into digital signals. The data acquisition system 180 then sends the detection data, which have been now converted in digital signals, to a console device 300 (including a processing unit 350 (described later)). By the way, it may be so configured that the reconstruction processor 350b (described later) executes reconstruction-processing on the detection data, which are gathered by the data acquisition system 180, in a short time so as to generate a CT image in real time. In this case, accordingly, the data acquisition system 180 is configured to shorten the time required for gathering detection data.

(Patient Table)

The patient table 200 is a device used for supporting and moving the subject E, which is the object to be scanned. The patient table 200 comprises a bed 210 and a bed drive 220. The bed 210 comprises a couch top 230, on which the subject E is placed, and a pedestal 240, which supports the couch top 230. The couch top 230 is configured to be translated by the bed drive 220 in the rostrocaudal direction of the subject E and in the direction perpendicular to the rostrocaudal direction. In other words, the bed drive 220 drives the couch top 230, which supports the subject E, to move into and move out of the opening 130a of the rotating body 130. The pedestal 240 is configured to allow the bed drive 220 to move the couch top 230 in the up and down direction (i.e., a direction perpendicular to the rostrocaudal direction of the subject E). By the way, the patient table 200 may take a configuration that does not include the couch top 230. In other words, the X-ray CT system as this embodiment can include a configuration in which the gantry apparatus 100 is moved with respect to the patient table 200.

(Console Device)

The console device 300 is used for inputting instructions to the X-ray CT system 1. In addition, the console device 300 includes a function of reconstructing CT image data (tomographic data and volumetric data), which represent internal structures of the subject E, based on the detection data gathered by the gantry apparatus 100. The console device 300 is configured to include an input unit 310, a display unit 320, a scanning-control unit 330, a setup unit 340, a processing unit 350, a storage 360, a display controller 370, and a main controller 380.

<Input Unit>

The input unit 310 is used as an input device to the console device 300 for execution of various operations. The input unit 310 is configured to include, for example, a key-board, a mouse, a track ball, and a joystick. In addition, as the input unit 310, a GUI may be used with the display unit 320.

<Display Unit>

The display unit 320 may comprise any type of displaying device like an LCD or a CRT display, and it displays various X-ray CT images. For example, tomographic images, volume-rendering images, MPR images, etc. are displayed on the display screen of the display unit 320. In addition, the display unit 320 may be configured to display a viewing box for an MPR image.

Furthermore, the display unit 320 displays a setup screen (not shown) for setting scanning conditions, an operation screen for executing scanning with the gantry apparatus 100, a setup screen for inputting various parameters used for reconstruction-processing, and a setup screen for setting window levels and window widths. In addition, in a case where control parameters for a contrast-agent injector are set by the input unit 310, the display unit 320 may be configured to display a setup screen for this kind of setting. In addition, the display unit 320 displays a respiration waveform and a specification screen for specifying a particular phase of the respiration wave. A specification operation made herein generates specification information, which is described later.

Moreover, in a case where the input unit 310 is configured at least partly to constitute a GUI, the display unit 320 displays items constituting the GUI. For example, the display unit 320 displays a setup screen for setting scanning conditions and parameters for reconstruction-processing, image-processing, etc. as part of the GUI. In addition, the display unit 320 displays an operation window in GUI for activation of the gantry and the bed. The display unit 320 also displays an operation screen in GUI for specifying ranges for contrast-enhanced images, non-contrast-enhanced images, subtraction images, etc.

<Control Unit>

The scanning-control unit 330, the setup unit 340, the processing unit 350, the display controller 370, and the main controller 380 comprise such processing units as CPUs, GPUs, and ASICs, which are not shown in the drawings, and such storage devices as ROMs, RAMs, and HDDs, which are also not shown in the drawings. Some storage devices include control programs stored therein for execution of functions of respective parts, and the processing units, for example, CPUs, execute the respective programs, which are stored in the storage devices, for realizing the functions of respective parts.

<Scanning-Control Unit>

The scanning-control unit 330 controls various actions involved in scanning with X-rays. The scanning-control unit 330, upon receiving an instruction for starting scanning, which has been instructed, for example, with the input unit 310 through the main controller 380, starts scanning with the gantry apparatus 100. In other words, the scanning-control unit controls the high voltage generator 140, the gantry drive 170, the collimator drive 150, and the bed drive 220 in accordance with preset X-ray radiation conditions, fields of view, scanning ranges, scanning modes, and slice thicknesses.

The X-ray conditions include parameters for X-ray generation, which X-rays are used for irradiation. These parameters are, for example, the tube current (mA), the tube voltage (kV), and the rotational speed of the X-ray tube (in the rotating body 130), and the scanning duration, which parameters are all related to X-ray generation. In one example according to this embodiment, the scanning-control unit 330 radiates X-rays intermittently. In other words, the scanning duration herein includes, in periodic scanning, both the duration from the starting point in time to the ending point in time for the scanning session and the duration from this ending point to the starting point of the next scanning session. The scanning duration is predetermined by the setup unit 340, which is described later. In addition, the scanning-control unit 330 receives an instruction for starting X-ray radiation at the timing of a phase that is set by the setup unit 340, and the scanning-control unit starts scanning.

In other words, the scanning-control unit 330 receives an instruction for starting a predetermined X-ray radiation, from the setup unit 340, and the control unit starts X-ray radiation as instructed. How the instruction for starting X-ray radiation is set is described later.

The parameters for fields of view include control parameters for actions of the X-ray collimator 160, which is controlled by the gantry drive 170. The reconstruction conditions include reconstruction functions, reconstruction intervals, etc. The scanning modes are, for example, scanning methods (conventional scanning, helical scanning, etc.). The parameters for helical scanning include helical pitch, which is defined by, for example, conditions for the movement of the couch top 230 driven by the bed drive 220 (action speed, amount of displacement, etc.).

For example, the scanning-control unit 330 controls the bed drive 220 in accordance with the information set for the X-ray scanning range. Under the control, the bed drive 220 moves the bed 210 at a predetermined traveling velocity and by a predetermined amount of displacement. In addition, the scanning-control unit 330 controls the high voltage generator 140 in accordance with the information set for X-ray conditions. Under the control, the high voltage generator 140 supplies a high voltage to the X-ray generator 110 at a predetermined interval.

In addition, the scanning-control unit 330 controls the gantry drive 170 in accordance with the information set for the rotational speed of the rotating body 130. Under the control, the gantry drive 170 drives the rotating body 130 to rotate at a predetermined velocity. Furthermore, the scanning-control unit 330 controls the collimator drive 150 in accordance with the information set for the fields of view, etc. Under the control, the collimator drive 150 drives the X-ray collimator 160 and controls the range of X-ray radiation. In addition, the scanning-control unit 330 controls the bed drive 220 in accordance with the setup information for the scanning mode. Under the control, the bed drive 220 moves the bed 210 at a predetermined traveling velocity and by a predetermined amount of displacement.

<Processing Unit>

The processing unit 350 executes various types of processing on the detection data received from the gantry apparatus 100 (i.e., from the data acquisition system 180). The processing unit 350 is configured to include a preprocessor 350a, a reconstruction processor 350b, and an image generator 350c.

The preprocessor 350a executes such preprocessing as logarithmic transformation, offset correction, sensitivity correction, and beam hardening correction on the detection data, which have been detected with the gantry apparatus 100 (i.e., the X-ray detector 120), and the preprocessor generates projection data.

The reconstruction processor 350b executes reconstruction-processing on the projection data, which have been generated by the preprocessor 350a. The reconstruction-processing is executed in accordance with the reconstruction conditions, which are received from the setup unit 340 through the main controller 380. For tomographic data reconstruction, an arbitrary method can be employed including, for example, two-dimensional Fourier transformation and convolution back projection. Volumetric data are generated by interpolating a plurality of sets of tomographic data, which have been reconstructed. For volumetric data reconstruction, an arbitrary method can be employed including, for example, cone-beam reconstruction, multi-slice reconstruction, and magnified reconstruction. In a case where an X-ray detector having a multi-line configuration is employed as described above, volumetric data that cover a wide range can be constructed based on the data acquired by the volumetric scanning.

The image generator 350c executes image-processing on the tomographic data or the volumetric data, which have been generated by the reconstruction processor 350b, and generates X-ray CT image data. For example, the volumetric data are subjected to such rendering processing as MPR, Surface Rendering (SR), Shaded Surface Display (SSD), Volume Rendering (VR), Maximum Intensity Projection (MIP), Minimum Intensity Projection (MinIP), etc. Furthermore, the image generator 350c executes such image-processing as image-sharpening, noise reduction and suppression, signal-to-noise ratio improvement, and contour highlighting on the X-ray CT image data, which have been generated based on the tomographic data and the volumetric data.

<Setup Unit>

Figure 9:
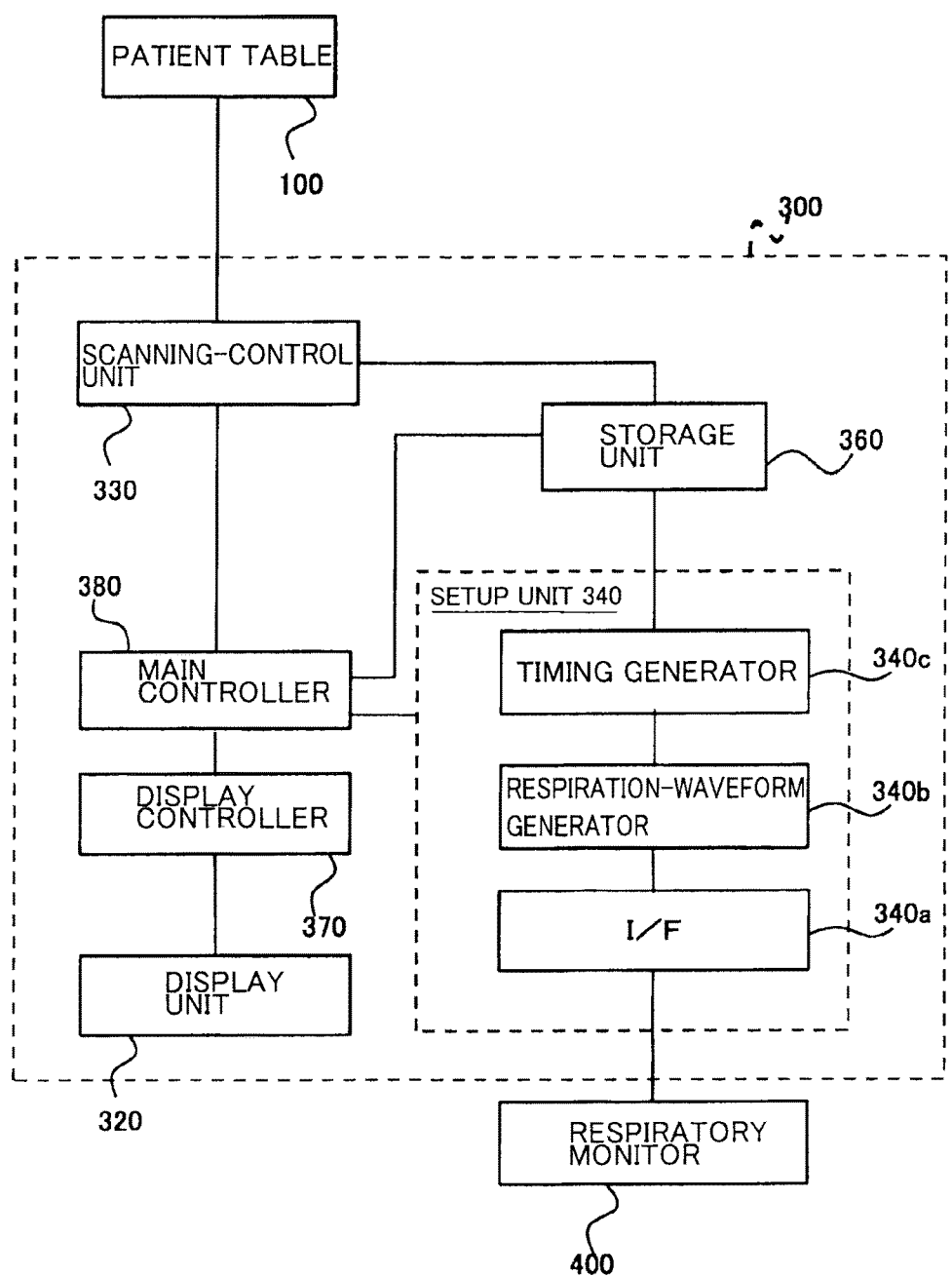
FIG. 9 is a block diagram showing a setup of the third embodiment.
Figure 10:
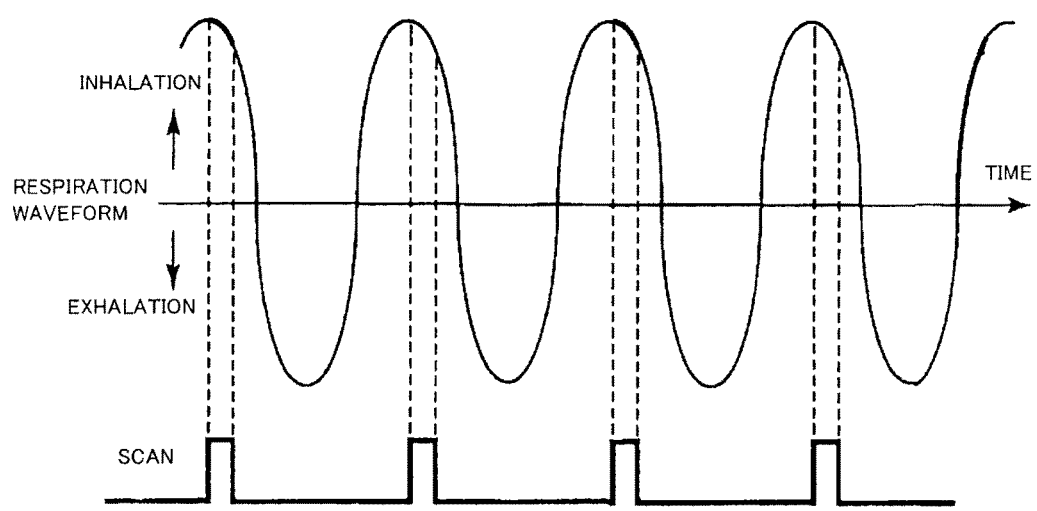
FIG. 10 is a schematic representation showing an example of respiration waveform and an example of timing for scanning, which is applied for the third embodiment.

Now, the setup unit 340 of the third embodiment is described with reference to FIGS. 9 and 10. FIG. 9 is a block diagram showing the schematic configuration of the setup unit 340 of the third embodiment. FIG. 10 is a schematic diagram showing an example of respiration wave of the subject, which is monitored by a respiratory monitor 400, and an example of timing for scanning. As shown in FIG. 9, the setup unit 340 is configured to include an I/F (interface) 340a, a respiration-waveform generator 340b, and a timing generator 340c.

The I/F 340a receives respiration-monitoring signals, which are output by the respiratory monitor 400. The respiratory monitor 400 captures the respiratory motion of the subject and outputs respiration-monitoring signals. The respiratory monitor 400 can be, for example, a band-like pressure sensor, which can be attached surrounding the abdomen of the subject. Another example can be an air-flow sensor, which measures the respiratory flow of the subject, or it may be a device that monitors, with a camera, an external region influenced by the breathing of the subject and that determines the motion by analyzing the monitored moving image.

The respiration-waveform generator 340b generates a respiration waveform as shown in FIG. 10 based on the respiration-monitoring signals received with the I/F 340a. The respiration waveform shown in FIG. 10 shows breathing levels with the horizontal axis representing time, and the vertical axis representing the depth of the respiration. In the drawing, the upward direction represents the height at inhalation level, and the downward direction represents the height at exhalation level. For example, when the respiration-waveform generator 340*b* receives a respiration-monitoring signal, it designates, from the waveform in the signal, the maximum value of the waveform as the maximum value at inhalation level (inhalation peak). Likewise, the respiration-waveform generator 340*b* designates the minimum value of the waveform as the maximum value at exhalation level (exhalation peak). In addition, the respiration-waveform generator 340*b* designates the mean value between the maximum value at inhalation level and the maximum value at exhalation level as the border value where the exhalation and the inhalation switch from one to the other.

Furthermore, the respiration-waveform generator 340*b* designates, from among the border values, the border value for the interval between a maximum value at inhalation level and the following maximum value at exhalation level as the end point for an inhalation period and as the start point for an exhalation period. Likewise, the respiration-waveform generator designates the border value for the interval between a maximum value at exhalation level and the following maximum value at inhalation level as the end point for an exhalation period and as the start point for an inhalation period.

In this way, the respiration-waveform generator 340*b* generates respiration waveform data and sends them to the display controller 370. The display controller 370 makes the display unit 320 display the respiration waveform received from the respiration-waveform generator 340*b*. The respiration-waveform generator 340*b* generates continuously the respiration waveform based on the respiration-monitoring signals received from the I/F 340*a* even after scanning-timing setup information, which will be described below, has been set up.

The timing generator 340*c* generates a timing for starting the X-ray radiation, which is generated by the X-ray generator 110 under the control of the scanning-control unit 330 in accordance with preset scanning-timing setup information, and it also generates information describing cycles (intervals) for X-ray radiation, which is under the control of the scanning-control unit 330. The following is a specific example.

The timing generator 340*c* reads out from the storage 360 the scanning-timing setup information, which has been preset by the user. The scanning-timing setup information may be set by the user on the display screen of the display unit 320 showing the respiration waveform. For example, a cursor is displayed together with the respiration waveform on the display unit 320 for the purpose of selecting an arbitrary phase of the respiration waveform. In this example, when the user selects an arbitrary phase of the respiration waveform with the input unit 310, this specification information is sent through the main controller 380 to the timing generator 340*c*.

Now, a case where the inhalation peak is set as the specification information is described. The timing generator 340*c*, upon receiving the specification information, identifies the phase specified for the respiration waveform by referring to the specification information and determines the maximum value at inhalation level for each waveform. Then, based on this information, the timing generator 340*c* determines the interval for the inhalation peaks. Furthermore, the timing generator 340*c* generates information indicating a cycle for X-ray radiation that corresponds to the interval. This cycle information is the information used for setting the time or interval from the starting point in time of a scanning session to that of the following scanning session in periodic scanning, which is controlled by the scanning-control unit 330.

In addition, the timing generator 340*c* generates exposure-time information on the basis of the respiration waveform. The exposure-time information indicates an exposure time for one scanning session in the above-mentioned periodic scanning. For example, the timing generator 340*c* sets the exposure time based on the time during which the degree of change at inhalation level in the respiration waveform remains within a predetermined range. Furthermore, the timing generator 340*c* makes the storage 360 store the cycle information and the exposure-time information. In addition, the timing generator 340*c* generates time-phase information that indicates the current time phase of the respiration, regarding the respiration waveform. Moreover, in consideration of the time-phase information and the specification information, the timing generator 340*c* generates a timing for starting X-ray radiation, i.e., an instruction for starting scanning, and the scanning-starting instruction generated here is sent to the scanning-control unit 330.

In this way, the timing generator 340*c* generates cycle information for X-ray radiation, X-ray exposure-time information, and a scanning-starting instruction (i.e., a timing for starting a first round of X-ray radiation). The scanning-control unit 330, upon receiving the scanning-starting instruction, starts X-ray radiation with the X-ray generator 110. In addition, the scanning-control unit 330, after having started the X-ray radiation, temporarily stops the radiation in accordance with the exposure-time information.

By the way, the specification information for setting these items of the scanning-setup information is not restricted to the maximum value at inhalation level (inhalation peak or maximum inhalation), and an arbitrary phase can be assigned including the maximum value at exhalation level (exhalation peak or maximum exhalation) and the mean value between the maximum value at exhalation level and that at inhalation level.

<Storage and Main Controller>

The storage 360 comprises such semiconductor memory devices as RAMs and ROMs. The storage 360 stores the detection data, the projection data, the X-ray CT image data, etc. The display controller 370 executes various controls concerning image display. For example, in response to an instruction for displaying above-mentioned various X-ray CT image data, the display controller 370 receives specific image data from the storage 360 and displays them in predetermined formats, and it also receives image data for the above-mentioned various setup screens and displays them in predetermined formats.

The main controller 380 controls the whole of the X-ray CT system 1 by controlling the actions of the gantry apparatus 100, the patient table 200, and the console device 300. For example, the main controller 380 controls the scanning-control unit 330 to make the gantry apparatus 100 execute preliminary scanning and main scanning and gather detection data. In addition, the main controller 380 controls the processing unit 350 to execute various types of processing on the detection data (preprocessing, reconstruction-processing, MPR processing, etc.). The main controller 380 also controls the display controller 370 to display X-ray CT images on the display unit 320 based on the image data stored in the storage 360.

[Actions]

Figure 11:
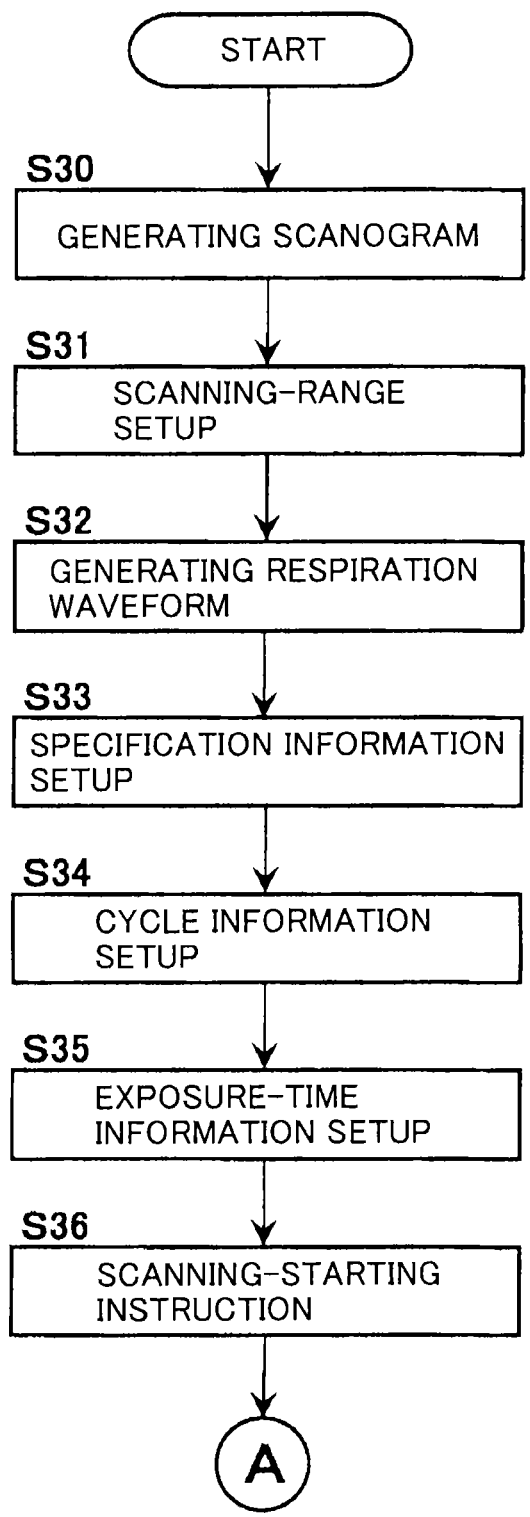
FIG. 11 is a flow chart showing an outline of actions taken by the X-ray CT system as a third embodiment.
Figure 12:
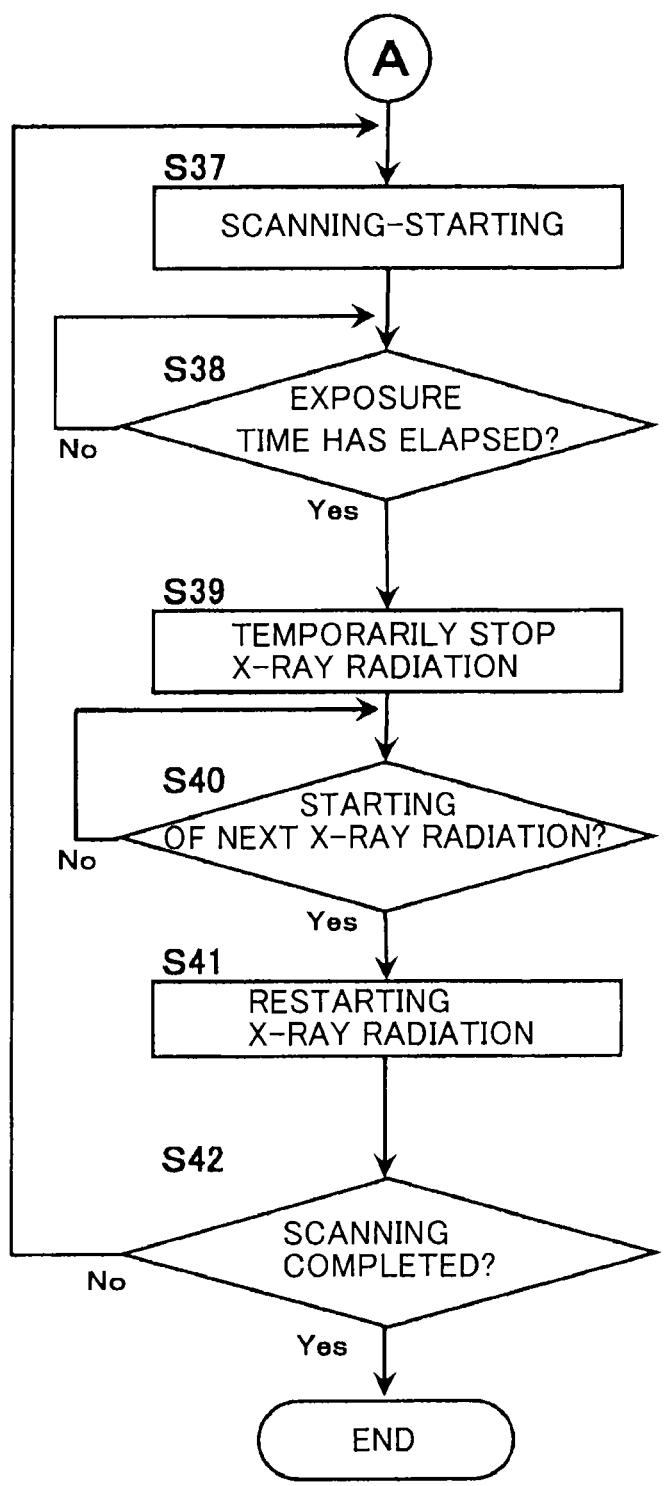
FIG. 12 is a flow chart showing another outline of actions taken by the X-ray CT system as a third embodiment.

Now, the actions of the X-ray CT system 1 as this embodiment are described with reference to FIGS. 11 and 12. FIGS. 11 and 12 are flow charts showing general actions of the X-ray CT system 1 as a third embodiment. Here, descriptions are given of the setting up of scanning-timing setup information, the generation of a scanogram, the instructing of starting scanning by the timing generator 340c, the periodic scanning performed by the gantry apparatus 100, and the completion of the scanning.

<S30>

The X-ray CT system 1 generates a scanogram before starting actual scanning. In other words, the scanning-control unit 330 controls the high voltage generator 140, the gantry drive 170, and the collimator drive 150 of the gantry apparatus 100 and the bed drive 220 in accordance with the preset scanning conditions, and the scanning-control unit takes a scanogram. For example, the scanning-control unit 330 controls the bed drive 220 for changing the relative position between the couch top 230 and the gantry apparatus 100, so that the subject is moved into scanning position. In addition, the scanning-control unit 330 controls the gantry drive 170 for moving the rotating body 130. In addition, the scanning-control unit 330 controls the high voltage generator 140 for scanning the subject at a single X-ray projection angle. The data acquisition system 180 gathers detection data that are based on X-rays that have passed through the subject. The gathered data are sent to the console device 300, and the processing unit 350 generates a scanogram based on the gathered data, which have been received by the console device 300.

By the way, the scanning-range setup screen of this embodiment is not restricted to things that are based on the scanogram. The step of generating a scanogram may be, therefore, omitted.

<S31>

The display controller 370 generates a scanning-range setup screen in accordance with the scanogram and in the predetermined format, which is read out from the storage 360, and the display controller displays it on the display unit 320. On the scanning-range setup screen, scanning ranges are set with the input unit 310, for example, by the user. After each scanning range (i.e., Region of Interest or ROI) is set on the scanning-range setup screen in this way, the information of the scanning ranges is passed from the display controller 370 to the main controller 380 and is stored in the storage 360.

<S32>

The I/F 340a receives respiration-monitoring signals from the respiratory monitor 400. The respiration-waveform generator 340b generates a respiration waveform as shown in FIG. 10 based on the respiration-monitoring signals, which are received through the I/F 340a.

<S33>

When the user specifies an arbitrary phase on the screen showing the respiration waveform, on the display unit 320 by using the input unit 310, etc., this specification information is sent through the main controller 380 to the timing generator 340c.

<S34>

The timing generator 340c, upon receiving the specification information, determines the specified phase (for example, the maximum value at inhalation level) for each of the waves in accordance with the specification information and thereby determines the interval for the specified phase (for example, the interval between the inhalation peaks). Furthermore, the timing generator 340c generates cycle information for X-ray radiation in accordance with this interval.

<S35>

The timing generator 340c generates exposure-time information by setting a time that can be within the period during which the degree of change at inhalation (or exhalation) level of the respiration waveform remains within a predetermined range.

<S36>

The timing generator 340c also generates time-phase information to indicate the current time phase of the respiration, regarding the respiration waveform. Furthermore, the timing generator 340c generates a timing for starting X-ray radiation or a scanning-starting instruction, in consideration of the time-phase information and the specification information.

By the way, either one of the part of the sequence from the generation of a scanogram to the setting of a scanning range (from S30 to S31) and the part from the generation of a respiration waveform to the setting of cycle information (from S32 to S34) can precede the other, or they may be executed in parallel.

<S37>

The scanning-control unit 330, upon receiving a scanning-starting instruction through the main controller 380, controls the high voltage generator 140, the gantry drive 170, and the collimator drive 150 of the gantry apparatus 100, and the bed drive 220 for executing scanning.

<S38>

The scanning-control unit 330 determines whether or not the exposure time has elapsed as specified by the exposure-time information of the scanning-setup information (which includes the exposure-time information). If the result of the determination by the scanning-control unit 330 is that the exposure time has not ("No" at S38), then this process is repeated.

<S39>

If the result of the determination by the scanning-control unit 330 is that the exposure time has elapsed as specified ("Yes" at S38), then the scanning-control unit controls the X-ray generator 110 to temporarily stop the X-ray radiation.

<S40>

Suspending the scanning, the scanning-control unit 330 determines, by counting the time from the start of the last X-ray radiation, whether or not the starting time of the next X-ray radiation has arrived in accordance with the scanning-setup information (cycle information). The scanning-control unit 330 repeats this process as long as the predetermined time has not elapsed ("No" at S40).

<S41>

If the result of the determination by the scanning-control unit 330 turns to that the time for starting the next X-ray radiation has arrived ("Yes" at S40), then the scanning-control unit controls the X-ray generator 110 to restart the X-ray radiation.

<S42>

The main controller 380 of the gantry apparatus 100 determines whether or not an instruction for completion of the scanning has come through the input unit 310. As long as no such instruction has input ("No" at S42), the main controller 380 repeats the above-mentioned steps S37-S42. In other words, the X-ray CT system 1 continues the scanning. On the other hand, if such an instruction is input ("Yes" at S42), the X-ray CT system 1 stops the scanning.

Operation and Effects

Now, the operation and effects are described of the X-ray CT system 1 as a third embodiment, which has been described above.

The X-ray CT system 1 as this embodiment generates cycle information, exposure-time information, and a scanning-starting timing when an arbitrary phase of a respiration waveform is specified on the display screen showing the respiration waveform. The X-ray CT system, therefore, can make uniform the shape and size of a region in displayed images without requiring any complicated operations in a case where fluoroscopy is performed for the region, whose shape and size are being changed under the influence of the breathing.

Fourth Embodiment

Figure 13:
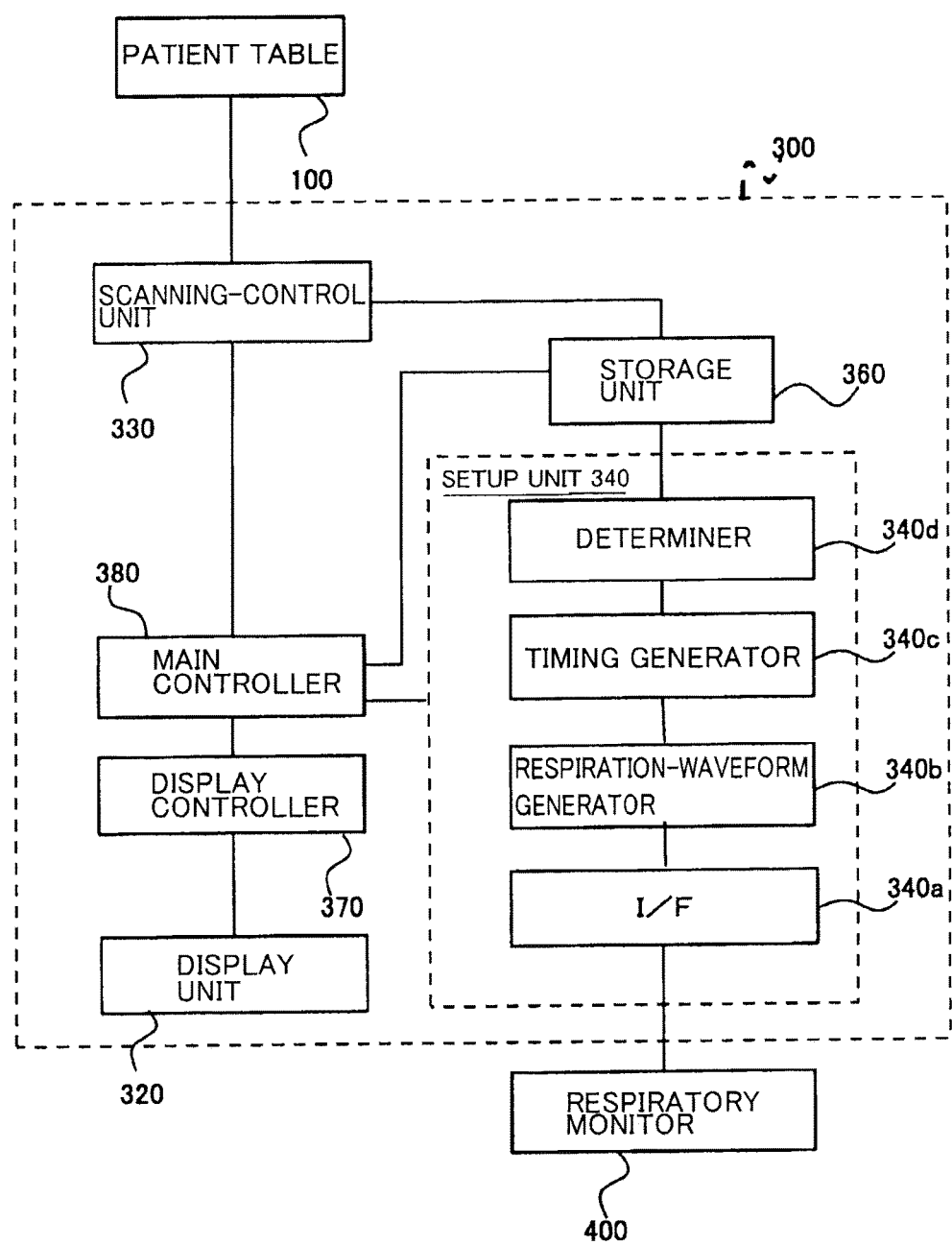
FIG. 13 is a block diagram showing a setup unit as a fourth embodiment.

Now, an X-ray CT system 1 as a fourth embodiment is described with reference to FIG. 13. FIG. 13 is a schematic block diagram showing an outline of a setup unit 340 in the fourth embodiment. The fourth embodiment differs from the third embodiment in the processing, etc. performed by the setup unit 340. In relation to the differences, the actions and processing steps of some parts may be also different. The other parts are the same as the X-ray CT system 1 as a third embodiment. The following describes mainly differences from the third embodiment.
[Outline]
In the X-ray CT system 1 as a fourth embodiment, the setup unit 340 further comprises a determiner 340d. The determiner 340d compares a second respiration waveform with a first respiration waveform and determines whether there is a divergence or not. Here, the first respiration waveform is the respiration waveform that functions as a base for the scanning-setup information. The second respiration waveform, on the other hand, represents each of the respiration waves that have been generated sequentially since a scanning-starting instruction was generated by the timing generator 340c. The determiner 340d displays the result of the determination.
<Respiration-Waveform Generator>
The respiration-waveform generator 340b continuously generates the respiration waveform as shown in FIG. 10 even after a scanning-starting instruction has been generated by the timing generator 340c, based on the respiration-monitoring signals being received through the I/F 340a.
<Determiner>
The determiner 340d receives a second respiration waveform from the respiration-waveform generator 340b after a scanning-starting instruction has been made. The determiner also reads out the first respiration waveform from the storage 360, and then it compares the second respiration waveform with the first respiration waveform and displays the result of the comparison. The result of the comparison is shown as numerical information representing the amount of divergence or as ratio of divergence. The determiner 340d may overlay the first respiration waveform with the second respiration waveform in parallel with the displaying of X-ray CT images.

Operation and Effects

Now, the operation and effects are described of the X-ray CT system 1 as a fourth embodiment, which has been described above.
The X-ray CT system 1 as this embodiment generates cycle information, exposure-time information, and a scanning-starting timing, in response to the specification of an arbitrary phase of a respiration waveform on the display screen showing the respiration waveform. In this way, for fluoroscopy of a region whose shape and size are being changed under the influence of the breathing, the X-ray CT system can make uniform the shape and size of the region in displayed images without requiring any complicated operations.

There is a case, however, where the respiratory cycle may experience a change after the scanning has been started. For example, there may be a change in the respiratory cycle due to a fit of coughing of the subject. In such a case, the respiratory cycle can diverge from the preset scanning cycle, and there may be a change in the shapes and sizes of organs, etc. in the generated images in comparison with the images immediately before or the previously scanned images. In this regard, in the X-ray CT system 1 as this embodiment, the determiner 340d of the setup unit 340 compares the second respiration waveform with the first respiration waveform and displays the result of the comparison. In this way, the user can easily recognize the divergence of the respiratory cycle from the scanning cycle during the scanning. As a result, the user can make a decision promptly with regard to, for example, if a need has arisen for resetting the scanning-setup information. In such a case, unnecessary scanning can be avoided, and unnecessary radiation exposure can be prevented.

Fifth Embodiment

Figure 14:
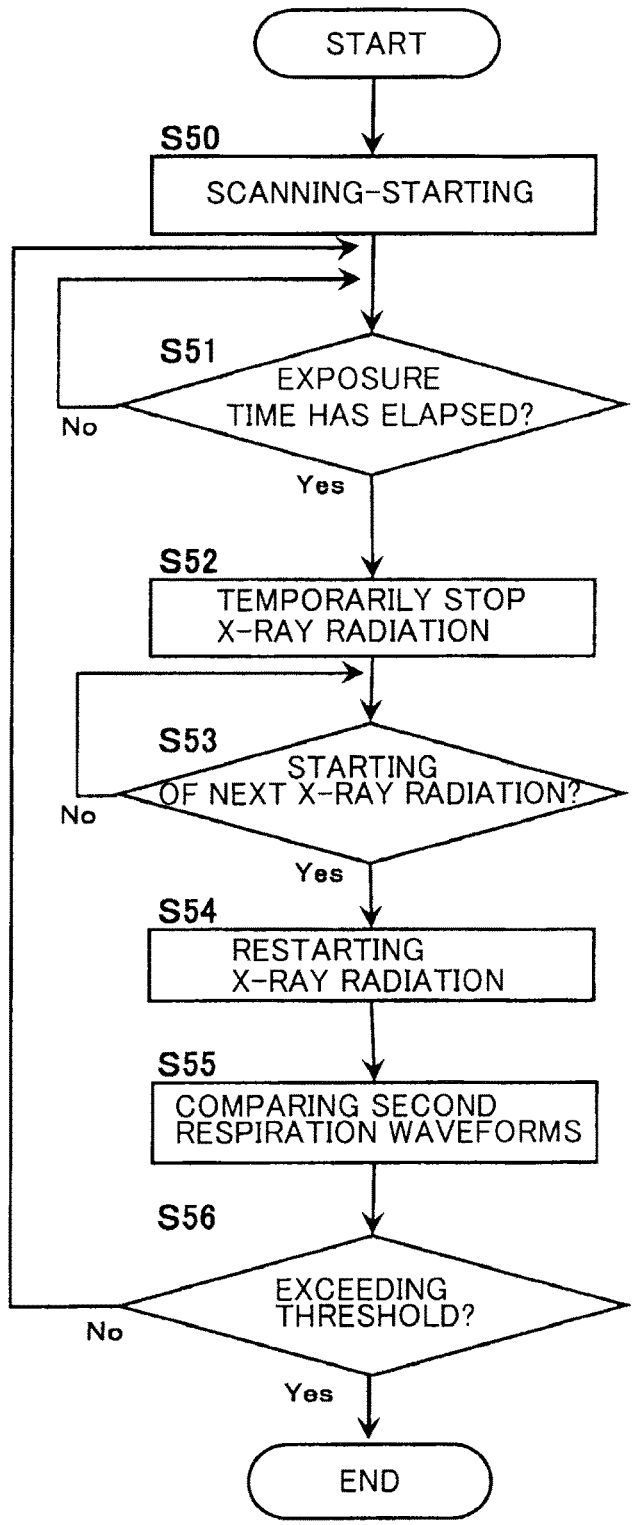
FIG. 14 is a flow chart showing general actions taken by an X-ray CT system as a fifth embodiment.

Now, an X-ray CT system 1 as a fifth embodiment is described with reference to FIG. 14. In the fifth embodiment, processes executed by the setup unit 340 are different from those of the third embodiment. In accordance with the differences, the actions and processing steps of some parts may be different. The other parts are the same as the X-ray CT system 1 as a fourth embodiment. The following describes mainly differences from the fourth embodiment.
[Outline]
In the X-ray CT system 1 as a fifth embodiment, the setup unit 340 further comprises a determiner 340d. The determiner 340d compares the second respiration waveform with the first respiration waveform and determines whether there is a divergence. Here, the first respiration waveform is the respiration waveform that has functioned as a base for the scanning-setup information. The second respiration waveform, on the other hand, represents each of the respiration waves that have been generated sequentially since the scanning-starting instruction has been made by the timing generator 340c. The determiner 340d stops the scanning being executed by the gantry apparatus 100 as a result of the determination if the divergence exceeds a preset threshold value or if it reaches the threshold value.
<Determiner>
The determiner 340d receives a second respiration waveform from the respiration-waveform generator 340b after a scanning-starting instruction has been made. The determiner 340d also reads out the first respiration waveform from the storage 360 and then compares the second respiration waveform with the first respiration waveform. The determiner 340d has a threshold value for the amount of divergence of the second respiration waveform from the first respiration waveform. With this threshold value, the determiner 340d determines whether or not the amount of divergence of the second respiration waveform from the first respiration waveform has reached the threshold value or it has exceeded the threshold value. If the result of the determination by the determiner 340d is that this condition has been satisfied, then it sends an instruction for stopping the scanning to the main controller 380. In response to the instruction, the main controller 380 stops the scanning, which has been executed by the gantry apparatus 100. In other words, it stops the actions of the X-ray generator 110, the gantry drive 170, and the collimator drive 150.

[Actions]

Now, the actions of the X-ray CT system 1 as this embodiment are described with reference to FIG. 14. FIG. 14 is a flow chart showing general actions of the X-ray CT system 1 as a fifth embodiment. Here, no descriptions are given of the setting up of scanning-timing setup information, the generation of a scanogram, and the instructing of starting scanning by the respiration-waveform generator 340b, because they are the same as those of the third embodiment. Descriptions given here, therefore, concern processes from the starting of periodic scanning to the completion of the scanning.

<S50>

The scanning-control unit 330, upon receiving a scanning-starting instruction through the main controller 380, controls the high voltage generator 140, the gantry drive 170, and the collimator drive 150 of the gantry apparatus 100, and the bed drive 220 for scanning.

<S51>

The scanning-control unit 330 determines whether or not the exposure time has elapsed as specified by the exposure-time information of the scanning-setup information (which includes the exposure-time information). If the result of the determination by the scanning-control unit 330 is that the exposure time has not elapsed as specified ("No" at S51), then this process is repeated.

<S52>

If the result of the determination by the scanning-control unit 330 is that the exposure time has elapsed ("Yes" at S51), then the scanning-control unit temporarily stops the X-ray radiation by controlling the X-ray generator 110.

<S53>

Suspending the scanning, the scanning-control unit 330 determines, by counting the time from the start of the last X-ray radiation, whether or not the starting time of the next X-ray radiation has arrived in accordance with the scanning-setup information (cycle information). The scanning-control unit 330 repeats this process (with "No" at S53) until the predetermined time has elapsed.

<S54>

If the result of the determination by the scanning-control unit 330 turns to that the time for starting the next X-ray radiation has arrived ("Yes" at S53), then the scanning-control unit controls the X-ray generator 110 to restart the X-ray radiation.

<S55>

The determiner 340d reads out the first respiration waveform from the storage 360 and compares the second respiration waveform with the first respiration waveform.

<S56>

The determiner 340d, then, determines whether or not the amount of divergence of the second respiration waveform from the first respiration waveform has reached the threshold value or it has exceeded the threshold value. If the result of the determination by the determiner 340d is that this condition has not been satisfied yet ("No" at S56), then processes S51-S56 are repeated. In other words, the X-ray CT system 1 continues the scanning. On the other hand, if the result of the determination by the determiner 340d is that this condition has been satisfied ("Yes" at S56), then the determiner sends a scanning-stopping instruction to the main controller 380. In response to the instruction, the main controller 380 stops the scanning, which has been executed by the gantry apparatus 100. For example, the actions of the X-ray generator 110, the gantry drive 170, and the collimator drive 150 are stopped. By the way, the above-mentioned processing steps S55 and S56 have been described as they follow processing step S54 for convenience. Processing steps S55 and S56, however, may be executed after the start of the scanning at step S50 and before step S54. Also in this embodiment, the scanning may be stopped with a scanning-stopping instruction received in the same way as in the other embodiments.

Operation and Effects

Now, the operation and effects are described of the X-ray CT system 1 as a fifth embodiment, which has been described above.

The X-ray CT system 1 as this embodiment generates cycle information, exposure-time information, and a scanning-starting timing when an arbitrary phase of a respiration waveform is specified on the display screen showing the respiration waveform. Consequently, in a case where fluoroscopy is performed for a region whose shape and size are being changed under the influence of the breathing, the X-ray CT system can make uniform the shape and size of a region in displayed images without requiring any complicated operations.

There may be a change in the respiratory cycle after the scanning has been started. For example, a fit of coughing by the subject may cause a change in the respiratory cycle. In such a case, the respiratory cycle can diverge from the preset scanning cycle, resulting in a change in the shapes and sizes of organs, etc. shown in the generated images in comparison with the images immediately before or the previously scanned images. In this regard, in the X-ray CT system 1 as this embodiment, the determiner 340d of the setup unit 340 compares the second respiration waveform with the first respiration waveform. As a result of the comparison, the determiner determines whether or not the amount of divergence between them has exceeded a threshold value. If the result of the determination is that the divergence has exceeded the threshold value, then the scanning is stopped. The user, therefore, easily recognizes the divergence of the respiratory cycle from the scanning cycle during the scanning. For example, in a case where there has arisen a need of resetting the scanning-setup information, unnecessary scanning may be avoided, and unnecessary radiation exposure can be prevented, before execution of meaningful scanning again.

The system can leave out the operation of instructing scanning-termination by the user, which results in an improved operability of the system for the user.

Variant Embodiment of the Fifth Embodiment

Now, a variant embodiment of the X-ray CT system 1 as a fifth embodiment is described. The X-ray CT system 1 as a fifth embodiment is configured such that after the second respiration waveform is compared with the first respiration waveform, if the result of the comparison is that the amount of divergence between the first and second respiration waveforms has exceeded a threshold value, the scanning being executed by the gantry apparatus 100 is stopped. The system, however, is not restricted to such a configuration, and it can be configured such that if the amount of divergence of the second respiration waveform from the first respiration waveform has exceeded the threshold value, then preset specification information (specifying an arbitrary respiratory phase) is read out, and the arbitrary respiratory phase (e.g., the maximum exhalation) may be specified of the second respiration waveform, in accordance with the specification information. On the basis of the newly specified arbitrary respiratory phase, new cycle information may be acquired for further scanning.

Sixth Embodiment

Figure 15:
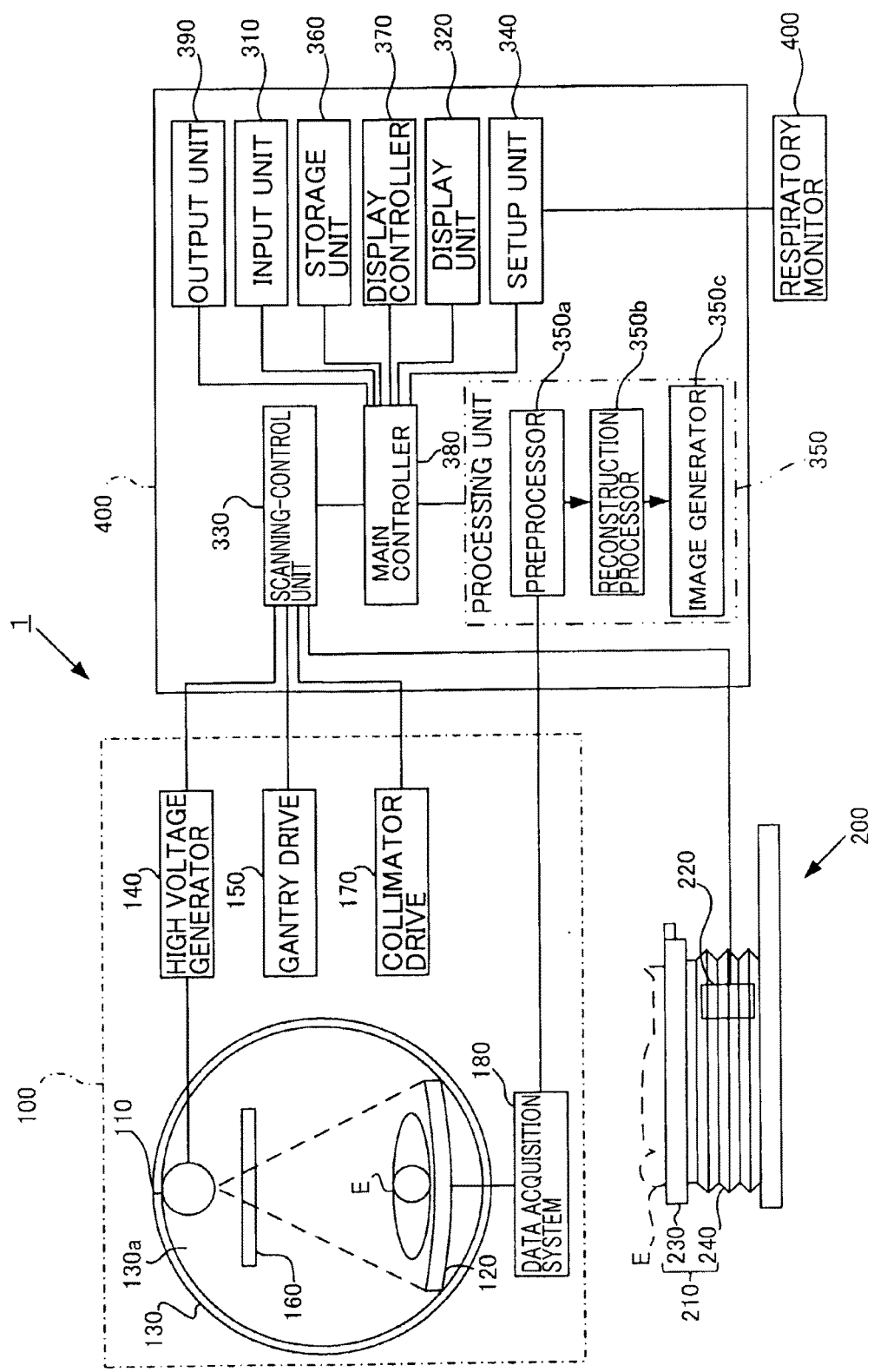
FIG. 15 is a schematic block diagram showing an outline of an X-ray CT system as a sixth embodiment.

Now, an X-ray CT system 1 as a sixth embodiment is described with reference to FIG. 15. FIG. 15 is a schematic block diagram showing an outline of the X-ray CT system 1 as a sixth embodiment. The sixth embodiment is different from the third embodiment in the configuration, etc. of the console device 300. In accordance with the differences, the actions and processing steps of some parts may be different. The other parts are the same as the X-ray CT system 1 as a fourth embodiment. The following describes mainly differences from the fourth embodiment.

[Outline]

In the X-ray CT system 1 as a sixth embodiment, the console device 300 of this embodiment is equipped with an output unit 390, for example, a speaker. The determiner 340*d* also compares the second respiration waveform with the first respiration waveform and determines whether or not there is divergence. If the result of the determination is that the divergence has exceeded a preset threshold value or has reached the threshold value, then the determiner 340*d* makes the main controller 380 output a voice of guidance with the output unit 390.

<Determiner>

The determiner 340*d* receives a second respiration waveform from the respiration-waveform generator 340*b* after a scanning-starting instruction has been made, and then it reads out the first respiration waveform from the storage 360. The determiner 340*d* compares the second respiration waveform with the first respiration waveform. The determiner 340*d* has a threshold value in memory for the amount of divergence of the second respiration waveform from the first respiration waveform. In accordance with this threshold value, the determiner 340*d* determines whether or not the amount of divergence of the second respiration waveform from the first respiration waveform has reached the threshold value or has exceeded the threshold value. If the result of the determination by the determiner 340*d* is that this condition has been satisfied, then the determiner sends an instruction for outputting a voice of guidance, to the main controller 380. In response to the instruction, the main controller 380 makes the output unit 390 output a voice of guidance.

<Output Unit>

The output unit 390 outputs a voice of guidance as a breathing instruction. For example, the main controller 380 reads out from the storage 360 a voice of guidance that urges the subject to take a breath with a predetermined depth, and the main controller makes the output unit 390 output it. The voice guidance can urge the subject to breathe consciously with different depths, for example, to do normal breathing (breathing at rest) or deep breathing.

The following explanation is an outline of an exemplary pattern of voice guidance data for breathing instructions, which are stored in the storage 360. After the determiner 340*d* has determined that the amount of divergence of the second respiration waveform from the first respiration waveform has reached a threshold value or has exceeded the threshold value, it sends the main controller 380 an instruction for outputting a voice of guidance as a breathing instruction. In response to the output instruction, for example, the main controller 380 at first reads out a predetermined set of voice guidance data from the storage 360. At this instant, based on the voice guidance data, the main controller 380 makes the output unit 390 output, for example, the guidance voice "Please make yourself comfortable". Since the guidance voice does not intentionally try to adjust the depth of the breathing of the subject, the subject continues normal breathing (breathing at rest).

In addition, the main controller 380 reads out a next set of voice guidance data from the storage 360 depending on the degree of divergence of the second respiration waveform from the first respiration waveform. Based on the voice guidance data, the main controller 380 makes the output unit 390 output, for example, the second necessary guidance "Breathe the air in as much as you can". This guidance voice urges the subject to take a deep breath and leads to the state of maximum inhalation.

After a predetermined time has elapsed since the main controller 380 read out the second set of voice guidance data, it reads out a next set of voice guidance data from the storage 360 as the third set of voice guidance data. At this instant, based on the voice guidance data, the main controller 380 makes the output unit 390 output the third necessary guidance "Breathe out the air as much as you can". This guidance voice urges the subject to breathe the air out as much as he or she can and leads to the state of maximum exhalation.

After a predetermined time has further elapsed since the main controller 380 read out the third set of voice guidance data, it reads out a next set of voice guidance data from the storage 360 as the fourth set of voice guidance data. At this instant, based on the voice guidance data, the main controller 380 makes the output unit 390 output the fourth necessary guidance "Once again, breathe the air in as much as you can". This guidance voice urges the subject to take a deep breath again and leads to the state of maximum inhalation, again.

Additionally, the main controller 380 may make the output unit 390 output the guidance "Please make yourself comfortable" again, based on the voice guidance data. This guidance voice urges the subject to have normal breathing (breathing at rest).

Operation and Effects

Now, the operation and effects are described of the X-ray CT system 1 as a sixth embodiment, which has been described above.

The X-ray CT system 1 as this embodiment generates cycle information, exposure-time information, and a scanning-starting timing when an arbitrary phase is specified of a respiration waveform on the display screen showing the respiration waveform. Consequently, in a case where fluoroscopy is performed for a region whose shape and size are being changed under the influence of the breathing, the X-ray CT system 1 can make uniform the shape and size of the region in displayed images without requiring any complicated operations.

There may be a change in the respiratory cycle after the scanning has been started. For example, a change can occur in the respiratory cycle due to a fit of coughing experienced by the subject. In such a case, the respiratory cycle can diverge from the preset scanning cycle, and there may be a change in the shapes and sizes of organs, etc. shown in generated images in comparison with the images taken immediately before or with the previously scanned images. In this regard, in the X-ray CT system 1 as this embodiment, the determiner 340*d* of the setup unit 340 compares the second respiration waveform with the first respiration waveform. As a result of the comparison, the determiner determines whether or not the amount of divergence between the waveforms has exceeded a threshold value. If it has exceeded the threshold value, then the determiner makes the output unit 390 output a voice. If the respiratory cycle of the subject has changed from that used as preset, during the scanning, then the respiratory cycle of the subject can be adjusted again with the guidance voices.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

REFERENCE NUMBERS IN DRAWINGS

Numeral 1 designates an X-ray CT system;
10, gantry apparatus;
11, X-ray generator;
12, X-ray detector;
13, rotating body;
14, high voltage generator;
15, gantry drive;
16, X-ray collimator;
17, collimator drive;
18, data acquisition system;
101, detector unit;
102, detection drive unit;
30, patient table;
31, top plate;
32, top-plate drive unit;
40, console device;
41, control unit;
411, information recorder;
412, information selector;
413, drive controller;
414, alarm controller;
42, scanning-control unit;
43, processing unit;
431, preprocessor;
432, reconstruction processor;
433, rendering processor;
434, section-position determiner;
435, image formation unit;
44, storage unit;
45, display unit; and
46, operation unit.

What is claimed is:

1. An X-ray CT system, comprising:
a memory configured to store, in advance, a predetermined time phase in a respiration waveform, cycle information indicating a cycle in which the predetermined time phase repeatedly appears in the respiration waveform, and a time during which a degree of change in the respiration waveform remains within a predetermined range from when the predetermined time phase appears, as an irradiation time;
an acquisition system configured to execute scanning on the subject with X-rays and to gather data;
a controller configured to control the acquisition system to start the scanning at a time when the predetermined time phase appears and irradiate X-rays during the irradiation time and stop irradiating X-rays after a lapse of the irradiation time until the predetermined time phase appears again repeatedly for the cycle;
an image generator configured to repeatedly generate images of the subject based on data gathered by the scanning;
an acquirer unit configured to acquire new cycle information in parallel with the scanning done by the acquisition system under control of the controller; and
a determiner unit configured to determine whether or not a difference between the cycle information stored in the memory and the new cycle information is within a preset range, wherein when the difference is within the preset range, the controller continues the scanning.

2. The X-ray CT system according to claim 1, wherein the memory stores the predetermined time phase, which is any one of a time phase at maximum exhalation, a time phase at maximum inhalation, and a time phase between the maximum exhalation and the maximum inhalation.

3. The X-ray CT system according to claim 2, wherein the memory stores time-phase information and the predetermined time phase, which is any one of a time phase at maximum exhalation, a time phase at maximum inhalation, and a time phase between the maximum exhalation and the maximum inhalation.

4. The X-ray CT system according to claim 1, wherein the memory stores the predetermined time phase, which is a time phase at maximum inhalation.

5. The X-ray CT system according to claim 4, wherein the memory stores time-phase information and the predetermined time phase, which is the time phase at maximum inhalation.

6. The X-ray CT system according to claim 1, further comprising a display configured to display the difference together with the images.

7. The X-ray CT system according to claim 1, wherein when the determiner unit has determined that the difference is not within the range, the controller makes the acquisition system stop the scanning.

8. X-ray CT system according to claim 1, wherein
when the determiner unit has determined that the difference is not within the range, the controller makes the acquisition system execute the scanning in accordance with the predetermined time phase and with the new cycle information.

9. The X-ray CT system according to claim 1, further comprising an output unit, wherein
the memory further stores guidance voice information for adjusting respiration of the subject, and
when the determiner unit has determined that the difference is not within the range, the controller controls the output unit to output a voice in accordance with the guidance voice information.

* * * * *